United States Patent
Poglitsch et al.

(10) Patent No.: US 9,684,004 B2
(45) Date of Patent: Jun. 20, 2017

(54) METHOD FOR MEASUREMENT OF PEPTIDIC DEGRADATION PRODUCTS OF A PROTEOLYTIC CASCADE IN BLOOD SAMPLES

(75) Inventors: Marko Poglitsch, Vienna (AT); Cornelia Schwager, Vienna (AT); Hans Loibner, Vienna (AT); Manfred Schuster, Vienna (AT)

(73) Assignee: ATTOQUANT DIAGNOSTICS GMBH, Vienna (AT)

( * ) Notice: Subject to any disclaimer, the term of this patent is extended or adjusted under 35 U.S.C. 154(b) by 0 days.

(21) Appl. No.: 14/396,201

(22) PCT Filed: Jun. 6, 2012

(86) PCT No.: PCT/EP2012/060678
§ 371 (c)(1),
(2), (4) Date: Oct. 22, 2014

(87) PCT Pub. No.: WO2013/182237
PCT Pub. Date: Dec. 12, 2013

(65) Prior Publication Data
US 2015/0050676 A1  Feb. 19, 2015

(51) Int. Cl.
*C12Q 1/56* (2006.01)
*G01N 33/86* (2006.01)
*G01N 33/68* (2006.01)

(52) U.S. Cl.
CPC ......... *G01N 33/86* (2013.01); *G01N 33/6842* (2013.01); *G01N 2333/515* (2013.01); *G01N 2333/81* (2013.01); *G01N 2333/96472* (2013.01); *G01N 2410/02* (2013.01); *G01N 2410/06* (2013.01)

(58) Field of Classification Search
CPC ............... G01N 33/86; G01N 33/6842; G01N 2333/515; G01N 2333/81; G01N 2410/02; G01N 2333/96472
USPC .......................................................... 435/13
See application file for complete search history.

(56) References Cited

FOREIGN PATENT DOCUMENTS

| EP | 2015073 | 1/2009 |
|---|---|---|
| WO | WO 2009/124330 | 10/2009 |
| WO | WO2010/017972 | 2/2010 |
| WO | WO2011/001029 | 1/2011 |

OTHER PUBLICATIONS

Van Kats et al. Intrarenal Angiotensin II: Interstitial and Cellular Levels and Site of Production; Kidney International, vol. 60 (2001) pp. 2311-2317.*
Elased et al. Brain Angiotensin-Converting Enzymes: Role of Angiotensin-Converting Enzyme 2 in Processing Angiotensin II in Mice; Experimental Physiology, vol. 93.5 (2008) pp. 665-675.*
Cui et al: "Simultaneous Analysis of Angiotensin Peptides by LC-MS and LC-MS/MS: Metabolism by Bovine Adrenal Endothelial Cells", *Analytical Biochemistry*, vol. 369, No. 1, pp. 27-33, Aug. 28, 2007.
Bystrom et al: "Plasma Renin Activity by LC-MS/MS: Development of a Prototypical Clinical Assay Reveals a Subpopulation of Human Plasma Samples with Substantial Peptidase Activity", *Clinical Chemistry*, vol. 56, No. 10, pp. 1561-1569, Aug. 2, 2010.
Nishiyama et al: "Relationship Between Biological Variation in B-Type Natriuretic Peptide and Plasma Renin Concentration in Stable Outpatients With Dilated Cardiomyopathy", *Official Journal of the Japanese Circulation Society*, http://www.j-circ.or.jp, Jun. 21, 2011.
Minghao Ye et al: "Murine Recombinant Angiotensin-Converting Enzyme 2 Effect on Angiotensin II-Dependent Hypertension and Distinctive Angiotensin-Converting Enzyme 2 Inhibitor Characteristics on Rodent and Human Angiotensin-Converting Enzyme 2", *Hypertension*, vol. 60, No. 3, pp. 730-740, Jul. 9, 2012.
Rice et al: "Evaluation of angiotensin-converting enzyme (ACE), its homologue ACE2and neprilysin in angiotensin peptide metabolism", *Biochem. J.*, Biochemical Society, vol. 383, pp. 45-51, Jul. 29, 2004.
Spanuth et al: English Abstract for CN 102124345, "D-Dimer, Troponin, NT-PROBNP for Pulmonary Embolism".

* cited by examiner

*Primary Examiner* — Scott Long
*Assistant Examiner* — Paul Martin
(74) *Attorney, Agent, or Firm* — Norton Rose Fulbright US LLP

(57) ABSTRACT

The invention discloses a method for measurement of peptidic degradation products of a proteolytic cascade (for example, the renin-angiotensin system (RAS) and the bradykinin system) in biological samples, especially blood samples, wherein the sample is incubated until a steady state equilibrium is reached for at least one peptidic degradation product involved in said proteolytic cascade and wherein said at least one peptidic degradation product in steady state equilibrium of the proteolytic cascade is quantified in the sample.

19 Claims, 27 Drawing Sheets

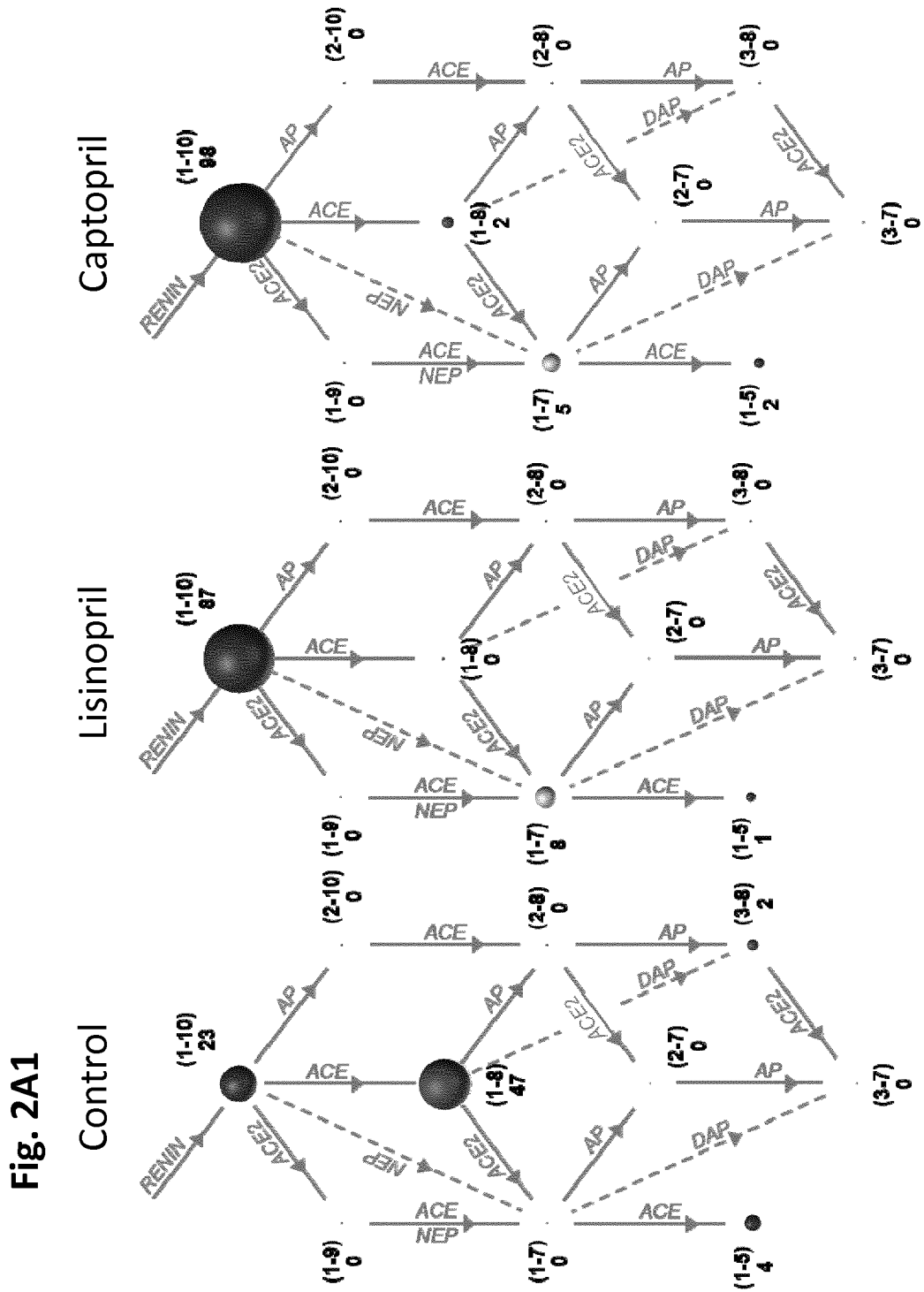
Fig. 2A1

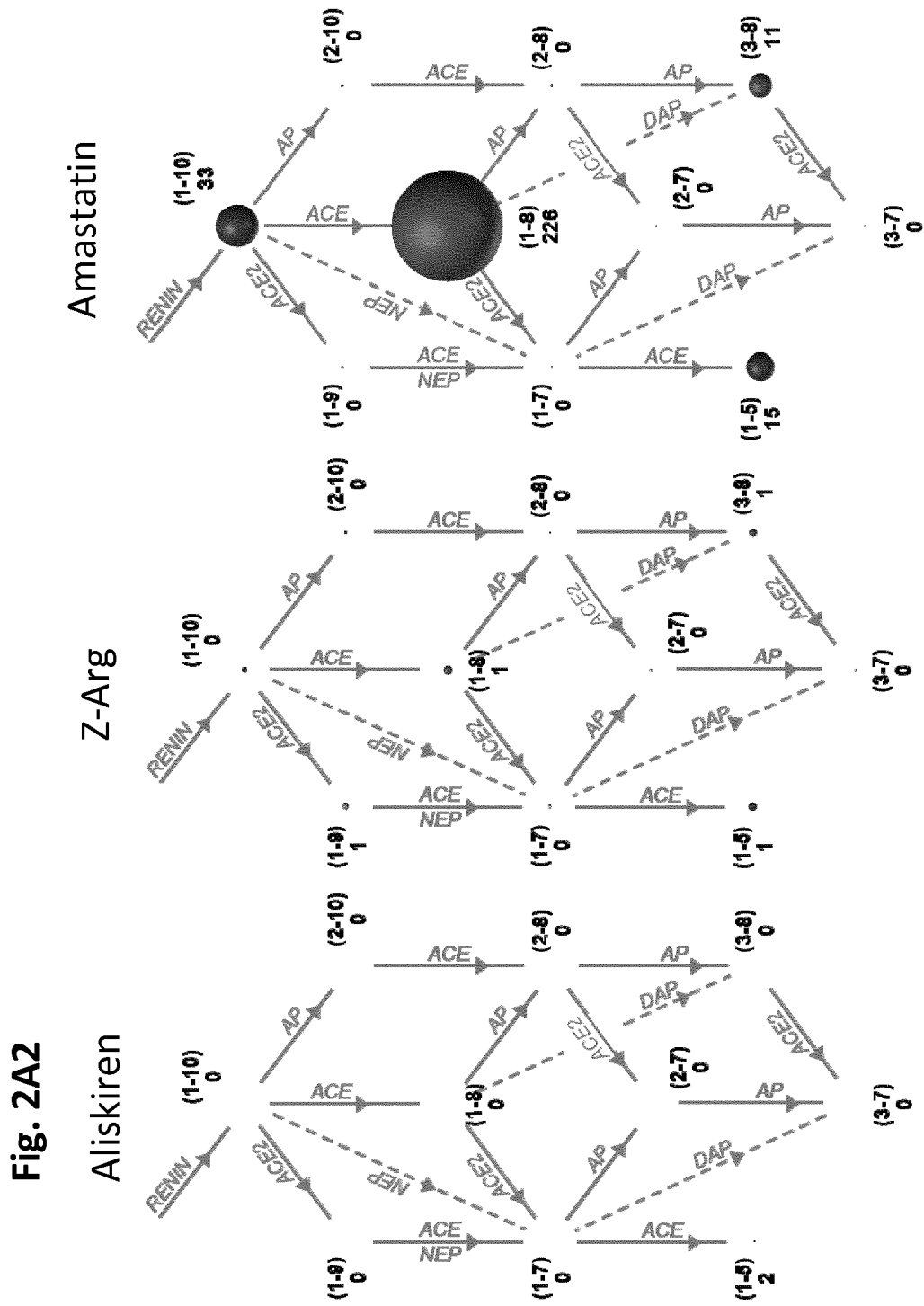
Fig. 2A2

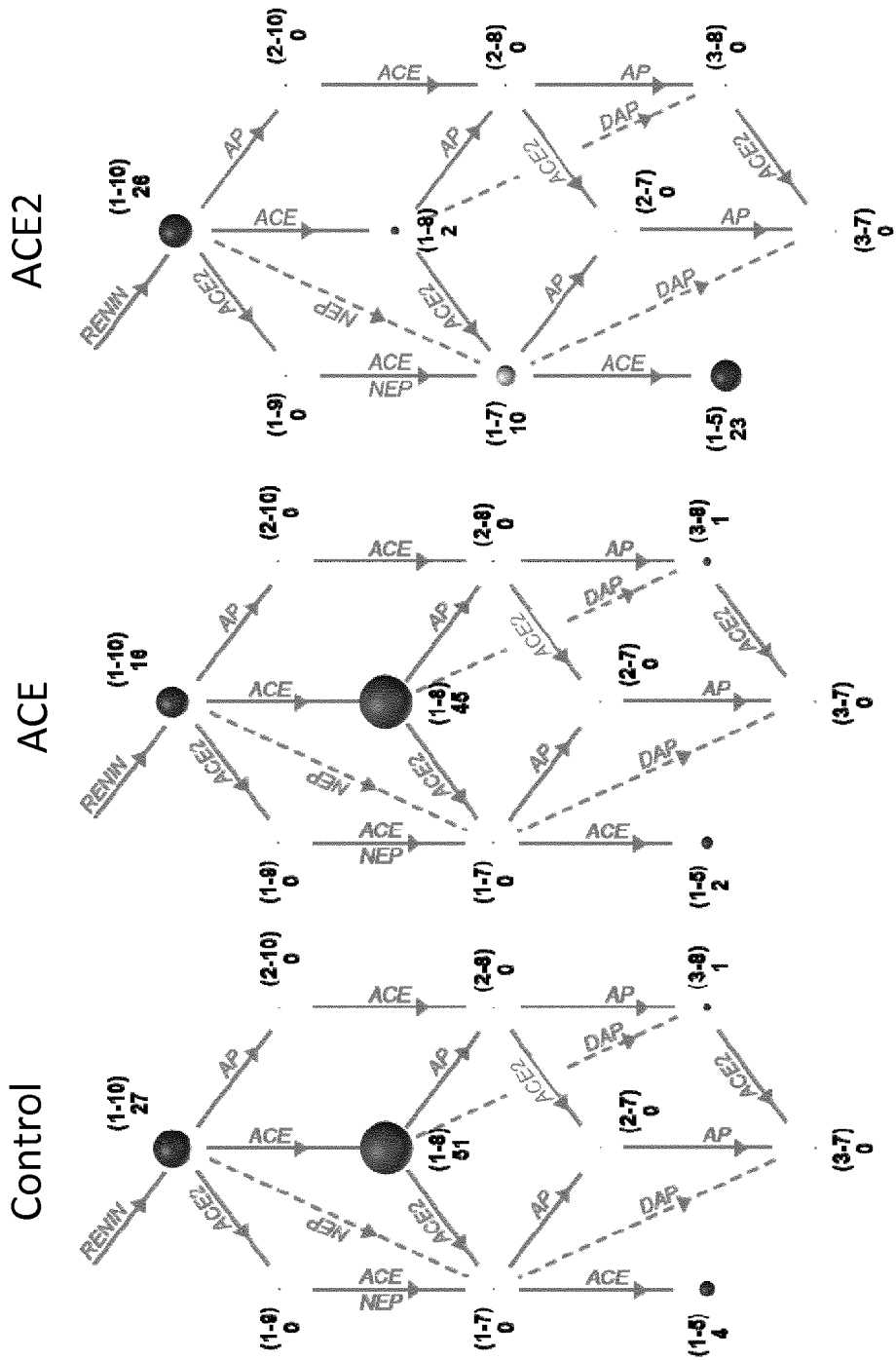
Fig. 2B1

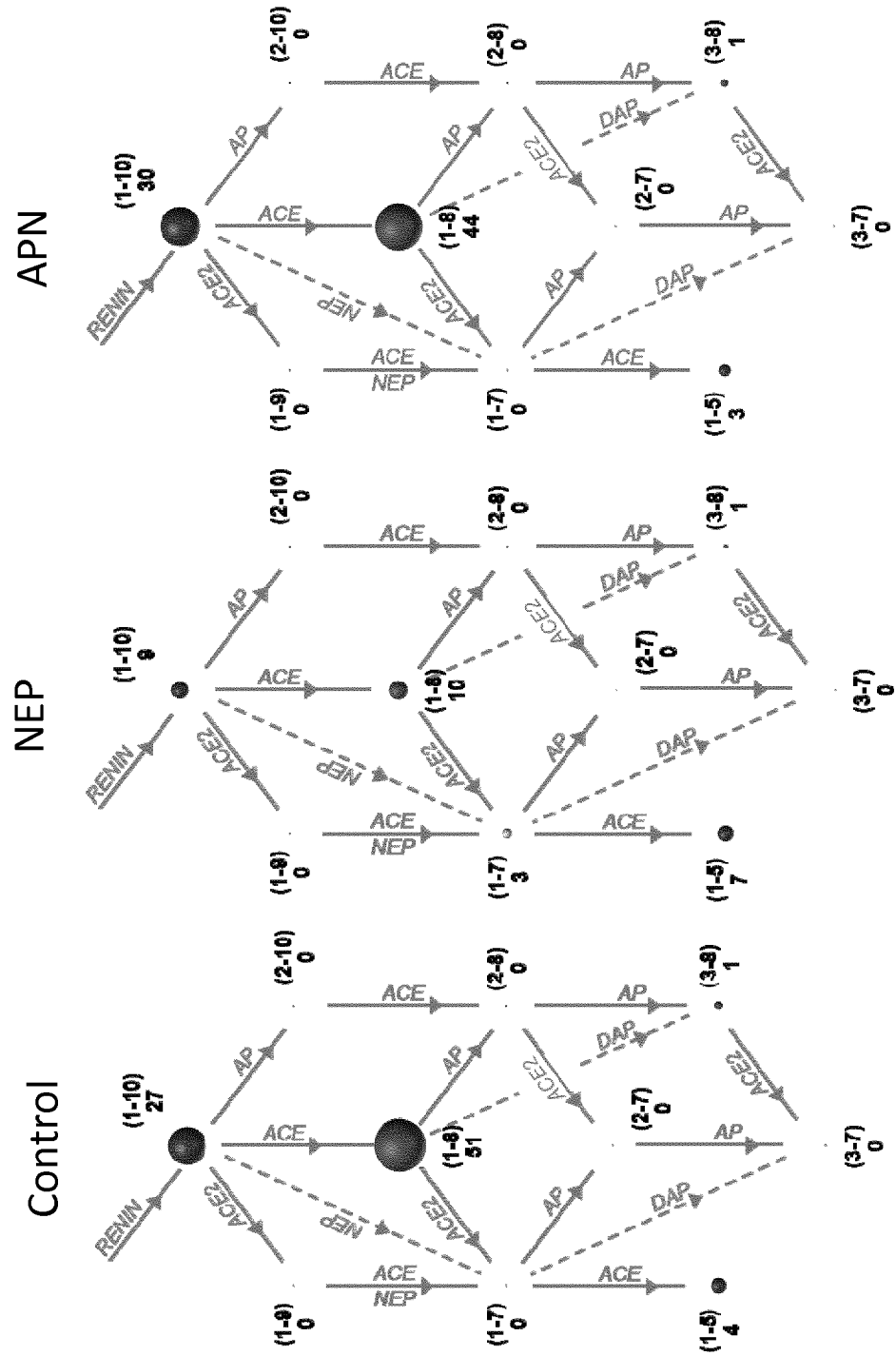
Fig. 2B2

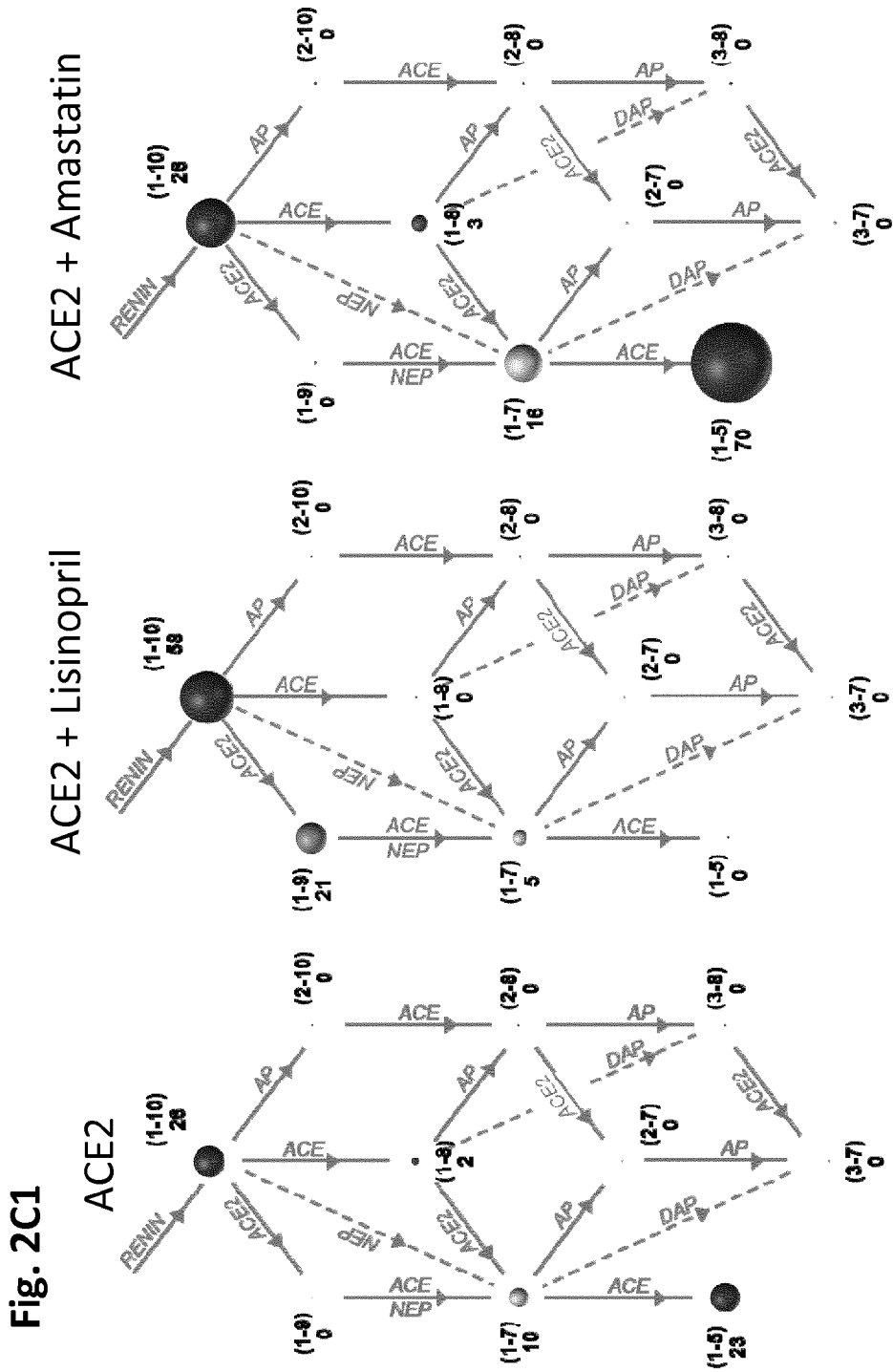
Fig. 2C1

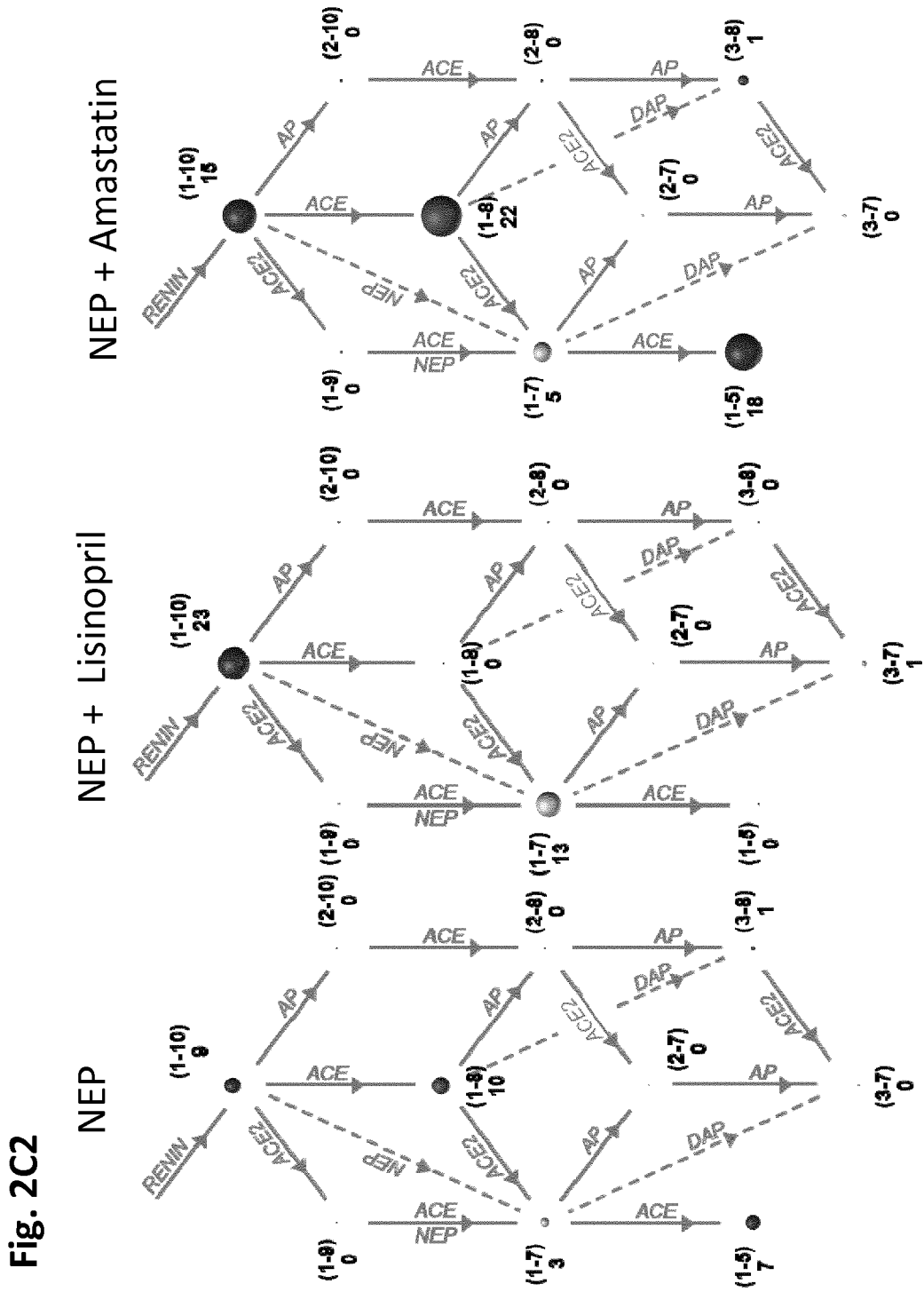
Fig. 2C2

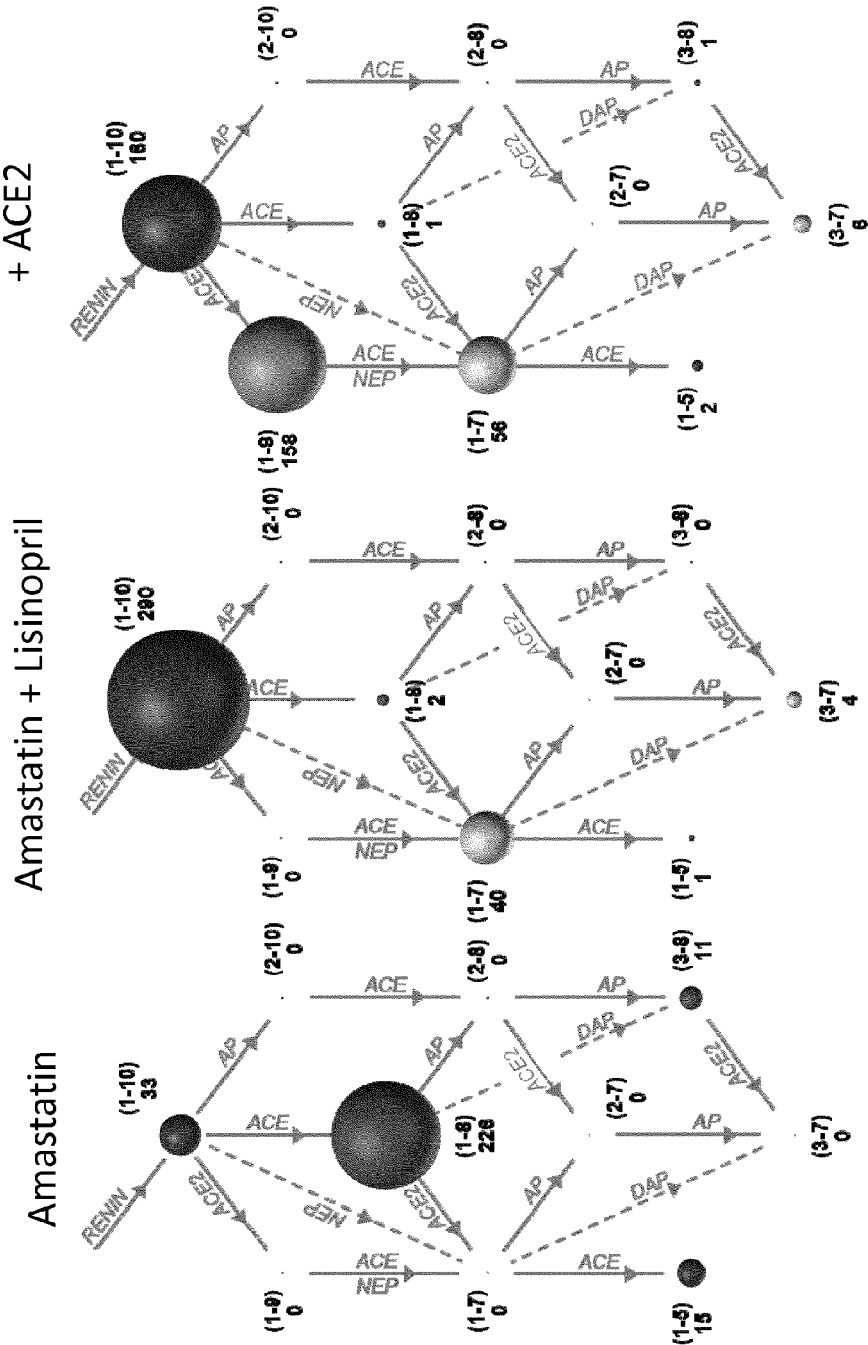
Fig. 2C3

Fig. 4B1

| | RAS-Fingerprint / Blood | | | |
|---|---|---|---|---|
| | Ang 1-8 | Ang 1-10 | | Molar Ratio |
| | [pg/ml] [fmol/ml] | [pg/ml] | [fmol/ml] | 1-8/1-10 [-] |
| 1 | 8 8 | 12 | 9 | 0,81 |
| 2 | 8 7 | 17 | 13 | 0,57 |
| 3 | 5 5 | 18 | 14 | 0,35 |
| 5 | 3 3 | 9 | 7 | 0,39 |
| 4 | 18 17 | 27 | 21 | 0,79 |
| 6 | 8 7 | 12 | 9 | 0,79 |
| 7 | 3 3 | 12 | 10 | 0,28 |
| 8 | bdl bdl | bdl | bdl | bdl |
| 9 | 7 7 | 19 | 15 | 0,47 |
| 10 | 12 12 | 24 | 18 | 0,64 |
| 11 | 3 3 | bdl | bdl | bdl |
| 15 | 6 6 | 22 | 17 | 0,33 |
| MEAN | 7 7 | 17 | 13 | 0,54 |
| SEM | 1 1 | 3 | 2 | 0,09 |

Fig. 4B2

| | RSSE-Fingerprint / Blood | | | | Molar Ratio |
|---|---|---|---|---|---|
| | Ang 1-8 | | Ang 1-10 | | 1-8/1-10 [-] |
| | [pg/ml] | [fmol/ml] | [pg/ml] | [fmol/ml] | |
| 1 | 180 | 172 | 22 | 17 | 10,2 |
| 2 | 164 | 156 | 39 | 30 | 5,2 |
| 3 | 129 | 123 | 36 | 27 | 4,5 |
| 5 | 142 | 136 | 34 | 26 | 5,2 |
| 4 | 270 | 258 | 76 | 59 | 4,4 |
| 6 | 242 | 231 | 15 | 11 | 20,5 |
| 7 | 284 | 271 | 30 | 23 | 11,9 |
| 8 | 277 | 265 | 17 | 13 | 20,4 |
| 9 | 206 | 197 | 51 | 39 | 5,0 |
| 10 | 227 | 217 | 33 | 25 | 8,6 |
| 11 | 110 | 105 | 13 | 10 | 10,5 |
| 15 | 225 | 215 | 31 | 24 | 9,0 |
| MEAN | 204 | 195 | 33 | 25 | 9,6 |
| SEM | 16 | 16 | 5 | 4 | 1,6 |

Fig. 4B3

| | RSSE-Fingerprint / Plasma | | | | Molar Ratio |
|---|---|---|---|---|---|
| | Ang 1-8 | | Ang 1-10 | | 1-8/1-10 [-] |
| | [pg/ml] | [fmol/ml] | [pg/ml] | [fmol/ml] | |
| 1 | 321 | 307 | 34 | 26 | 11,9 |
| 2 | 311 | 297 | 54 | 41 | 7,2 |
| 3 | 346 | 331 | 62 | 47 | 7,0 |
| 5 | 325 | 311 | 53 | 41 | 7,6 |
| 4 | 680 | 650 | 90 | 70 | 9,3 |
| 6 | 376 | 359 | 14 | 11 | 34,1 |
| 7 | 523 | 500 | 48 | 37 | 13,4 |
| 8 | 409 | 391 | 27 | 21 | 19,0 |
| 9 | 416 | 398 | 60 | 47 | 8,6 |
| 10 | 396 | 379 | 62 | 48 | 7,9 |
| 11 | 305 | 292 | 12 | 9 | 31,9 |
| 15 | 361 | 345 | 37 | 28 | 12,2 |
| MEAN | 397 | 380 | 46 | 35 | 14,2 |
| SEM | 30 | 28 | 6 | 5 | 2,6 |

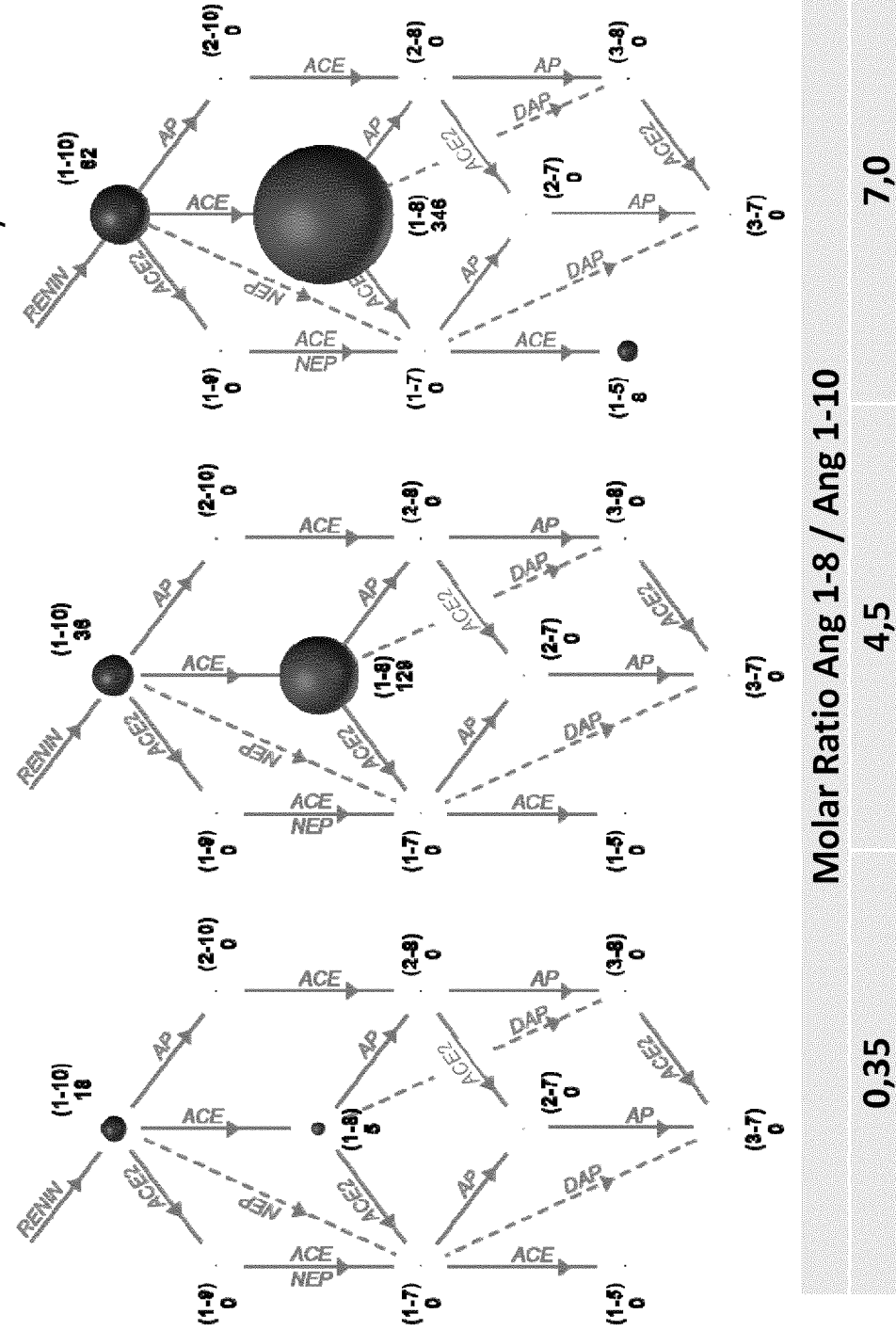
Fig. 4C1

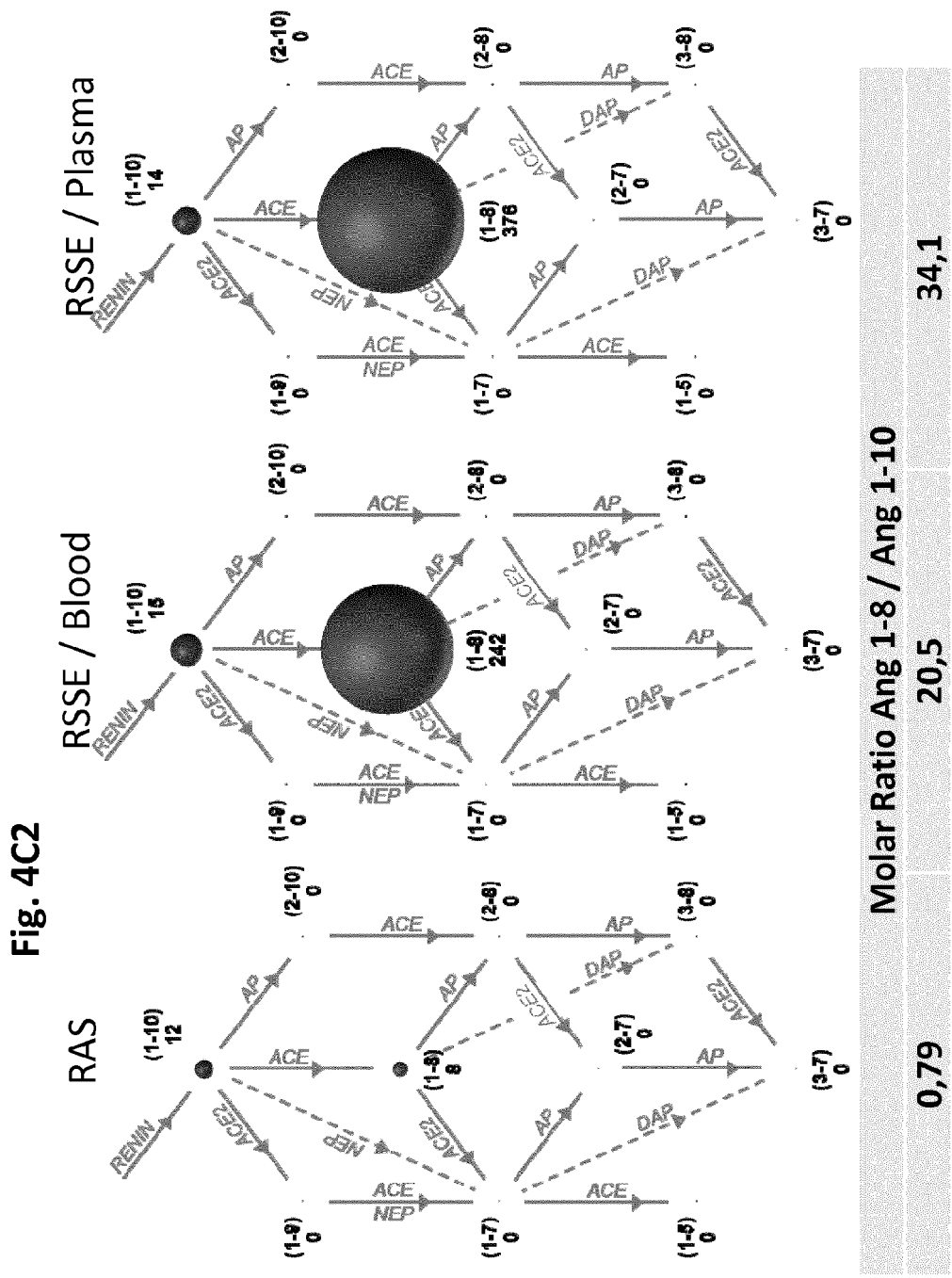
Fig. 4C2

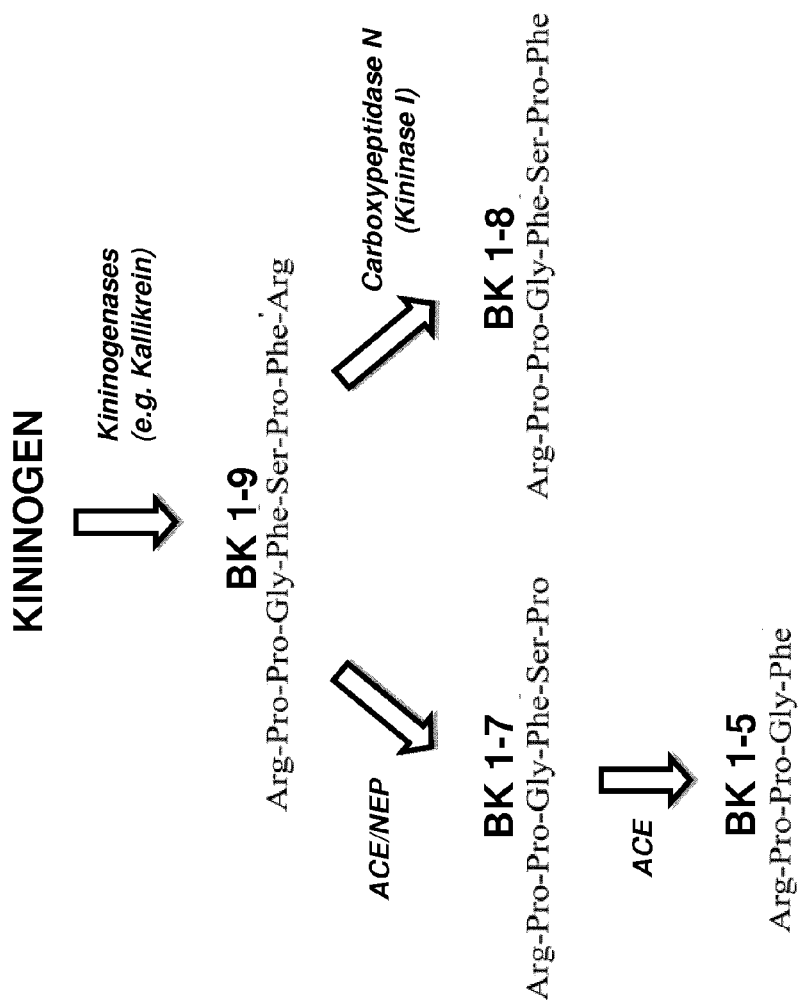

Fig. 6

Bradykinin-System

|  | [pg/ml] BK 1-9 | [pg/ml] BK 1-8 | [pg/ml] BK 1-7 | [pg/ml] BK 1-5 |
|---|---|---|---|---|
| T = 0 | 68 | 213 | 19 | 137 |
| T = 1h | 371 | 1256 | 56 | 114 |
| T = 3h | 357 | 1134 | 52 | 105 |

Renin-Angiotensin-System

|  | [pg/ml] Ang 1-10 | [pg/ml] Ang 1-8 | [pg/ml] Ang 1-7 | [pg/ml] Ang 1-5 | [pg/ml] Ang 2-8 | [pg/ml] Ang 3-8 | [pg/ml] Ang 2-7 | [pg/ml] Ang 3-7 | [pg/ml] Ang 1-9 | [pg/ml] Ang 2-10 |
|---|---|---|---|---|---|---|---|---|---|---|
| T = 0 | 18,3 | 18,1 | < | < | < | < | < | < | < | < |
| T = 1h | 145,4 | 291,2 | 7,0 | 10,0 | 12,0 | 8,9 | < | 2,3 | < | 9,0 |
| T = 3h | 133,1 | 257,9 | 7,8 | 8,0 | 13,0 | 11,5 | < | 1,7 | < | 10,1 |

Steady-State-Equilibrium Fingerprint of the Bradykinin-System

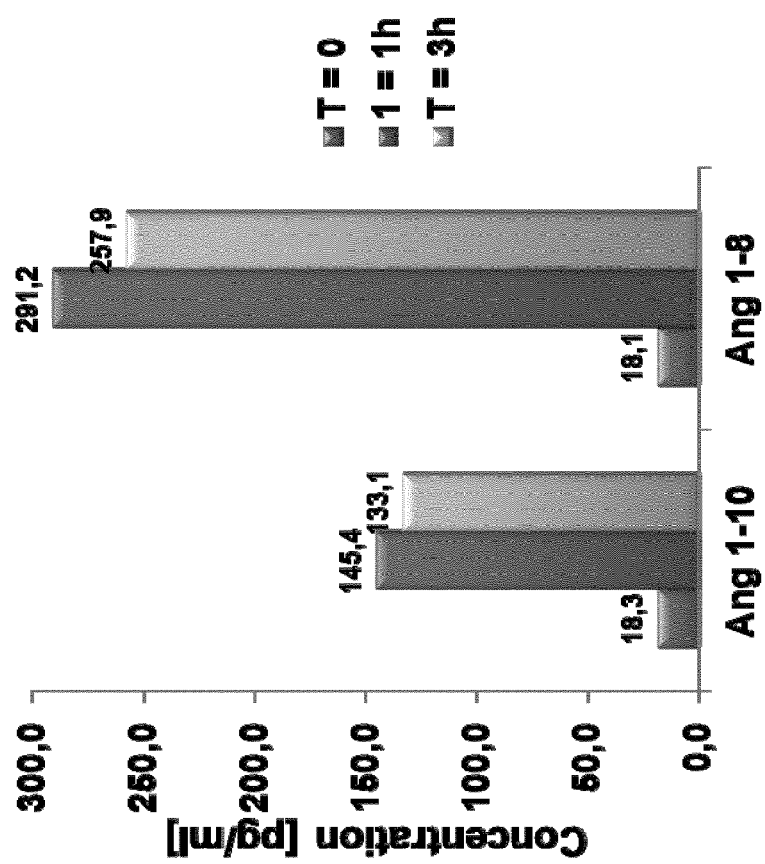
Fig. 7B1

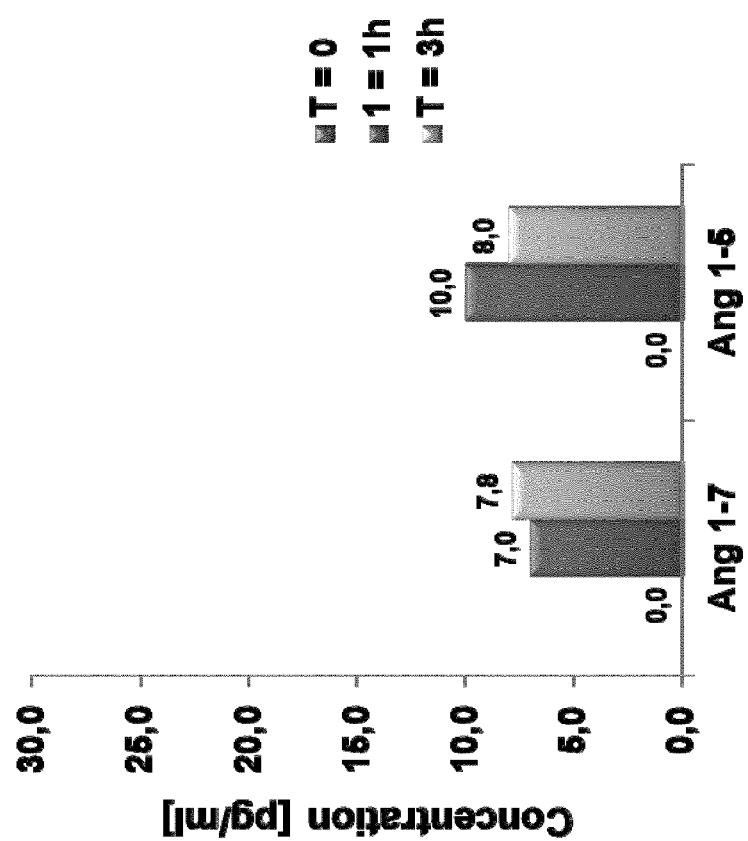
Fig. 7B2

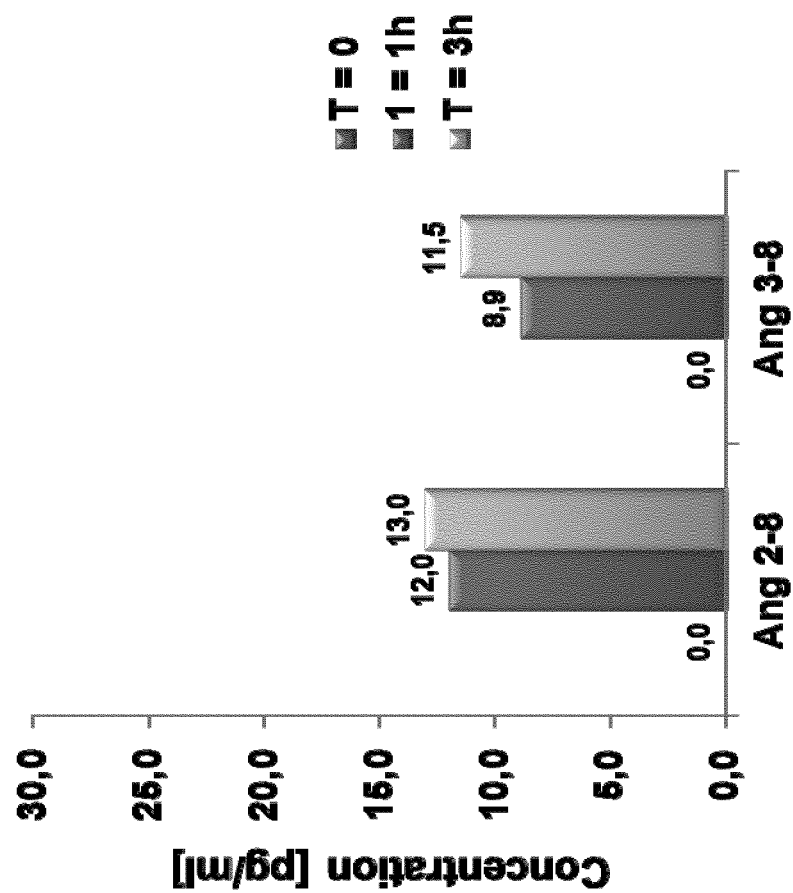
Fig. 7B3

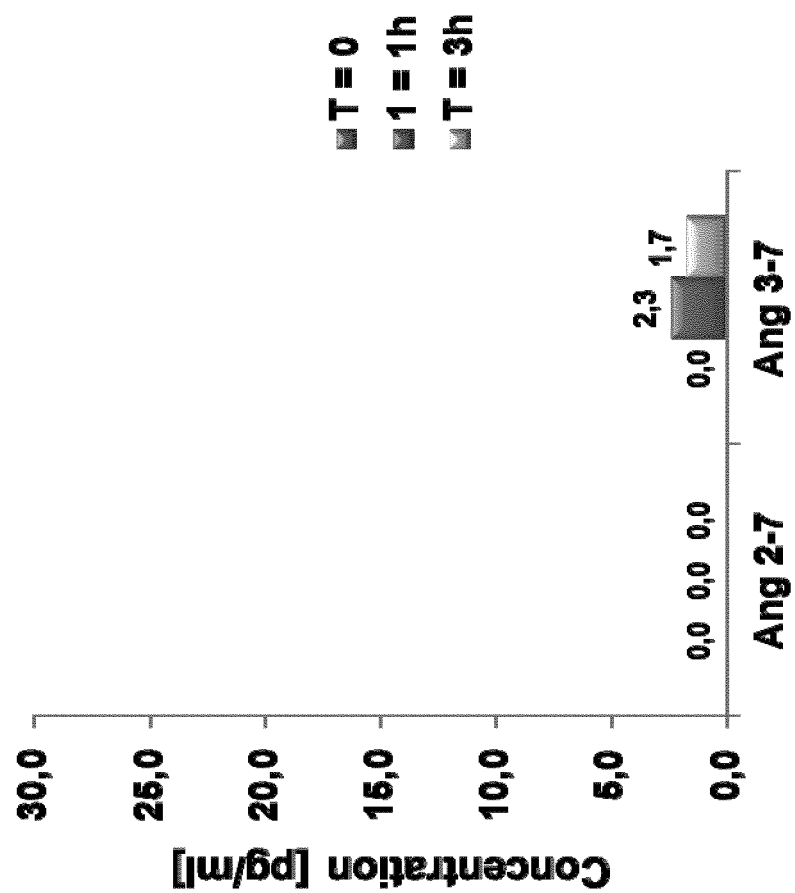

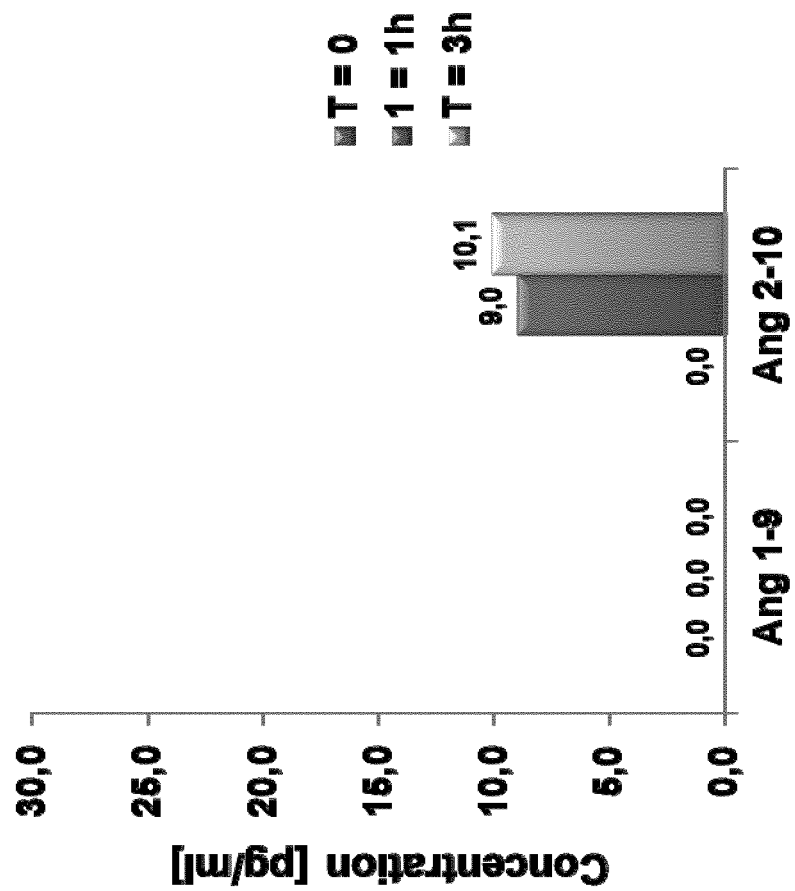

SEQUENCE LISTING

<160> NUMBER OF SEQ ID NOS: 14

<210> SEQ ID NO 1
<211> LENGTH: 10
<212> TYPE: PRT
<213> ORGANISM: Homo sapiens

<400> SEQUENCE: 1

Asp Arg Val Tyr Ile His Pro Phe His Leu
1               5                   10

```
<210> SEQ ID NO 2
<211> LENGTH: 8
<212> TYPE: PRT
<213> ORGANISM: Homo sapiens

<400> SEQUENCE: 2

Asp Arg Val Tyr Ile His Pro Phe
1               5

<210> SEQ ID NO 3
<211> LENGTH: 7
<212> TYPE: PRT
<213> ORGANISM: Homo sapiens

<400> SEQUENCE: 3

Asp Arg Val Tyr Ile His Pro
1               5

<210> SEQ ID NO 4
<211> LENGTH: 7
<212> TYPE: PRT
<213> ORGANISM: Homo sapiens

<400> SEQUENCE: 4

Arg Val Tyr Ile His Pro Phe
1               5

<210> SEQ ID NO 5
<211> LENGTH: 6
<212> TYPE: PRT
<213> ORGANISM: Homo sapiens

<400> SEQUENCE: 5

Val Tyr Ile His Pro Phe
1               5

<210> SEQ ID NO 6
<211> LENGTH: 5
<212> TYPE: PRT
<213> ORGANISM: Homo sapiens

<400> SEQUENCE: 6

Asp Arg Val Tyr Ile
1               5

<210> SEQ ID NO 7
<211> LENGTH: 9
<212> TYPE: PRT
<213> ORGANISM: Homo sapiens

<400> SEQUENCE: 7

Asp Arg Val Tyr Ile His Pro Phe His
1               5

<210> SEQ ID NO 8
<211> LENGTH: 6
<212> TYPE: PRT
<213> ORGANISM: Homo sapiens

<400> SEQUENCE: 8

Arg Val Tyr Ile His Pro
1               5

<210> SEQ ID NO 9
<211> LENGTH: 5
```

```
<212> TYPE: PRT
<213> ORGANISM: Homo sapiens

<400> SEQUENCE: 9

Val Tyr Ile His Pro
1               5

<210> SEQ ID NO 10
<211> LENGTH: 9
<212> TYPE: PRT
<213> ORGANISM: Homo sapiens

<400> SEQUENCE: 10

Arg Pro Pro Gly Phe Ser Pro Phe Arg
1               5

<210> SEQ ID NO 11
<211> LENGTH: 8
<212> TYPE: PRT
<213> ORGANISM: Homo sapiens

<400> SEQUENCE: 11

Arg Pro Pro Gly Phe Ser Pro Phe
1               5

<210> SEQ ID NO 12
<211> LENGTH: 8
<212> TYPE: PRT
<213> ORGANISM: Homo sapiens

<400> SEQUENCE: 12

Pro Pro Gly Phe Ser Pro Phe Arg
1               5

<210> SEQ ID NO 13
<211> LENGTH: 7
<212> TYPE: PRT
<213> ORGANISM: Homo sapiens

<400> SEQUENCE: 13

Arg Pro Pro Gly Phe Ser Pro
1               5

<210> SEQ ID NO 14
<211> LENGTH: 5
<212> TYPE: PRT
<213> ORGANISM: Homo sapiens

<400> SEQUENCE: 14

Arg Pro Pro Gly Phe
1               5
```

METHOD FOR MEASUREMENT OF PEPTIDIC DEGRADATION PRODUCTS OF A PROTEOLYTIC CASCADE IN BLOOD SAMPLES

This application is a national phase application under 35 U.S.C. §371 of International Application No. PCT/EP2012/060678 filed 6 Jun. 2012.

The present invention concerns the measurement of peptidic degradation products of a proteolytic cascade in blood samples.

The qualitative and quantitative occurrence of peptidic degradation products of proteolytic cascades in blood significantly varies with the physiologic or biochemical status of the subject. It may e.g. depend on the health status of the subject in relation to a given or suspected disease, and/or on medication, and/or other factors. The proteolytic degradation products mainly depend on the regulation and activity of proteolytic enzymes in the blood system which itself is dependent on the physiological status of the patient.

The renin-angiotensin system (RAS) is a proteolytic cascade, which is constituted by multiple enzymes and peptides. The cascade starts when angiotensin I (angiotensin 1-10 or Ang 1-10) is released from the pro-peptide angiotensinogen (AGT) by kidney secreted renin. AGT is abundantly expressed in the liver in humans and secreted into the circulation to constitute a virtually inexhaustible plasma pool of AGT. The peptide metabolites produced from Ang 1-10 by a variety of proteases act as ligands for angiotensin receptors in different tissues leading to a diversified panel of physiological functions mediated by angiotensin peptides.

The regulation of blood pressure is a well-studied physiological response affected by angiotensin peptides. Angiotensin II (angiotensin 1-8 or Ang 1-8) is produced by the proteolytic action of Angiotensin Converting Enzyme (ACE) by removing the two C-terminal amino acids from Ang 1-10. Ang 1-8 binds to cellular receptors leading to vasoconstriction and a consecutive increase in blood pressure.

This crucial role of ACE in the production of Ang 1-8, renders it a favourable pharmacologic target with the main focus of anti-hypertensive treatments set onto the reduction of Ang 1-8 levels leading to a decrease in blood pressure. This is also reflected by the broad panel of ACE inhibitors being in use for the treatment of hypertension. More recently other targetable RAS-enzymes including renin or neutral endopeptidase (NEP) were identified as pharmacologic targets for anti-hypertensive treatments while ACE inhibitors have been further optimised to decrease the frequency of side effects which are thought to be caused by a lack of ACE domain selectivity. Frequent side effects occurring during administration of ACE inhibitors include dry cough and angioedema and are thought to be caused by the inhibition of bradykinin (BK) degradation by these inhibitors as not only Ang 1-10 but also certain BK peptides are described to be cleaved by ACE.

Such limited substrate selectivity is a very common feature observed among RAS enzymes. Beside ACE, which is slightly different to other RAS enzymes because of its two-domain structure, also Angiotensin Converting Enzyme 2 (ACE2) is known to be able to cleave Ang 1-8 and Ang 1-10 to yield angiotensin 1-7 (Ang 1-7) and angiotensin 1-9 (Ang 1-9) respectively.

Furthermore, different RAS proteases can share their substrates leading to a competition of enzymes for a given substrate. For example, Ang 1-10 is known to be cleaved by ACE, ACE2, NEP and different aminopeptidases. All these considerations culminate in a very complex picture of the RAS, appearing as a meshwork of different enzymes, receptors and peptides leading to peptide concentrations affected by multiple factors.

Comparing published plasma levels of soluble ACE with Ang 1-10 plasma concentrations, it becomes clear that the ACE enzyme is present in significant molar excess compared to the Ang 1-10 peptide in circulation. This leads to a fail in describing the RAS by means of classic enzyme kinetics, which are based on the presence of a vast excess of substrate. At physiological conditions where angiotensin peptide levels in circulation do not exceed 10-200 fmol/ml, most enzymes are present in molar excess compared to their substrates forcing the investigator to step away from classical Menten-Kinetics to get a reliable view about biochemical processes at physiological conditions in the original sample matrix.

For example, Ang 1-10 has been described to be degraded by ACE2 with a much lower catalytic efficiency than Ang 1-8. Experiments showing this were performed in an artificial matrix using a vast excess of the substrates compared to the respective enzymes yielding maximal ACE2 conversion rate for Ang 1-8 to Ang 1-7 which is 65 times higher than the conversion rate for Ang 1-10 to Ang 1-9 [Rice et al., Biochem J., 383(2004), 45-51].

Taking together previous considerations with the fact that multiple angiotensin peptides show biologic activity, it becomes obvious that there is a big need for the evaluation of the RAS in biological samples ensuring the maintenance of physiological substrate concentrations in the sample. Manipulation of the RAS by pharmacologic means alters enzyme activities and peptide conversion rates at multiple levels of the system, which clearly favours the comprehensive assessment of the RAS for monitoring drug efficacy and inhibitor selectivity for defined enzyme reactions.

For example ACE inhibitors, which are described to inhibit both ACE domains to an unknown extent at physiological substrate concentrations, could be investigated for their inhibition of the conversion of Ang 1-10 to Ang 1-8, but also for their inhibitory potential regarding the conversion of Ang 1-7 to angiotensin 1-5 (Ang 1-5) or bradykinin 1-9 (BK 1-9) to bradykinin 1-7 (BK 1-7) or BK 1-7 to bradykinin 1-5 (BK 1-5) in order to optimise their side effect profiles.

Taking together published data for concentrations of angiotensin peptides and metabolising enzymes in human plasma, a great variance among different groups becomes obvious pointing to a low reproducibility of the used methods. Nevertheless, there is a vast molar excess reported for the pre-hormone AGT in human plasma compared to renin meaning that it serves as a very long-living source of Ang 1-10 which is produced by a constant renin activity in the plasma sample. This fact is also used in state-of-the-art PRA-Assays where the produced amount of Ang 1-10 over a defined time period is used to calculate back to the renin activity in the sample. Unfortunately, these values are frequently too low due to a lack of stabilisation (incomplete inhibition of degradation) of produced Ang 1-10, which requires a well-defined set of protease inhibitors to ensure that the degradation rate of Ang 1-10 is near zero [Bystrom et al., Clin. Chem. 56(2010), 1561-1569]. These pitfalls together with significant variances among donors result in a poorly reproducible procedure with only limited diagnostic value.

It is therefore an object of the present invention to provide a new and improved tool for analysing a subject's physiologic or biochemical status, especially the physiologic or biochemical status of a subject or human patient before, during and after a certain therapeutic treatment, including but not limited to drug administration, surgery or haemodialysis, by use of a blood sample of such subject.

Therefore, the present invention provides a method for measurement of peptidic degradation products of a proteolytic cascade in a biological sample, especially a blood sample, wherein the sample is incubated until a steady state equilibrium is reached for at least one peptidic degradation product involved in said proteolytic cascade and wherein said at least one peptidic degradation product in a steady state equilibrium concentration is quantified in the sample.

The term "steady state equilibrium" (SSE) as used herein means that the actual overall degradation rate of at least one peptidic degradation product involved in the proteolytic cascade is equal to the actual overall formation rate of said peptidic degradation product, thereby leading to a stable concentration of said peptidic degradation product, i.e. a steady state equilibrium peptide concentration which does not substantially vary over a certain time period, as further specified below. The actual overall formation rate of a peptidic degradation product is defined by the sum of the actual turnover rates of all enzymes involved in the formation of said peptidic degradation product, i.e. said peptidic degradation product is a direct product of said enzyme(s). The actual overall degradation rate of a peptidic degradation product is defined by the sum of the actual turnover rates of all enzymes involved in the degradation of said peptidic degradation product, i.e. said peptidic degradation product is a direct substrate of said enzyme(s).

The term "proteolytic cascade" as used herein shall mean a cascade comprising at least two consecutive proteolytic reactions. In one embodiment, the proteolytic cascade is a cascade of at least two, three, four, or five consecutive proteolytic reactions. Such proteolytic cascade may comprise at least 2, 3, 4, 5, 6, 7, 8, 9, 10, 11, 12, 13, 14, 15, 16, or 17 consecutive or non-consecutive proteolytic reactions, or combinations thereof, which may be branched or multiply branched. For example, proteolytic cascades according to the invention include the renin-angiotensin system (RAS), also called renin-angiotensin-aldosteron system (RAAS), the bradykinin system, the kinin-kallikrein system, the blood-clotting cascade, the complement system, apoptosis pathways, neuropeptide cascades (e.g. the oxytocin system), endothelin peptide cascades, and the natriuretic peptide cascades.

The terms "peptidic degradation product involved in the proteolytic cascade" or "peptidic degradation product of the proteolytic cascade" as used herein shall mean a peptide, which is part of said given proteolytic cascade, as substrate (precursor peptide) or product of at least one enzyme involved in the proteolytic cascade, or as substrate and product of at least two enzymes involved in the proteolytic cascade. Accordingly, for the RAS proteolytic cascade, peptides (or peptidic degradation products) involved in the proteolytic cascade may be selected from angiotensinogen, angiotensin I (Ang 1-10) and its biological degradation products, especially angiotensin I (Ang 1-10), angiotensin 2-10 (Ang 2-10), angiotensin II (angiotensin 1-8 or Ang 1-8), angiotensin III (angiotensin 2-8 or Ang 2-8), angiotensin IV (angiotensin 3-8 or Ang 3-8), angiotensin 1-9 (Ang 1-9), angiotensin 1-7 (Ang 1-7), angiotensin 2-7 (Ang 2-7), angiotensin 3-7 (Ang 3-7) and angiotensin 1-5 (Ang 1-5). For the bradykinin proteolytic cascade, peptides (or peptidic degradation products) involved in the proteolytic cascade may be selected from kallidin (KD or Lys-bradykinin) and its biological degradation products, especially bradykinin 1-9 (BK 1-9), bradykinin 2-9 (BK 2-9), bradykinin 1-8 (BK1-8), bradykinin 1-7 (BK 1-7) and bradykinin 1-5 (BK 1-5). In one embodiment, the one or more peptidic degradation products may be selected from peptides involved in one or more proteolytic cascades, e.g. from two or more proteolytic cascades, being either separate cascades or cascades that may be related or linked, e.g. by one or more identical or similar enzymes or peptides. In one embodiment, the proteolytic cascade is the renin-angiotensin system (RAS) or the bradykinin system, or both. For example, the one or more peptidic degradation products may be selected from the RAS and the bradykinin system. In one embodiment, the peptidic degradation product is selected from angiotensinogen, angiotensin I (Ang 1-10), angiotensin 2-10 (Ang 2-10), angiotensin II (angiotensin 1-8 or Ang 1-8), angiotensin III (angiotensin 2-8 or Ang 2-8), angiotensin IV (angiotensin 3-8 or Ang 3-8), angiotensin 1-9 (Ang 1-9), angiotensin 1-7 (Ang 1-7), angiotensin 2-7 (Ang 2-7), angiotensin 3-7 (Ang 3-7), angiotensin 1-5 (Ang 1-5), kallidin (KD or Lys-bradykinin), bradykinin 1-9 (BK 1-9), bradykinin 2-9 (BK 2-9), bradykinin 1-8 (BK1-8), bradykinin 1-7 (BK 1-7) and bradykinin 1-5 (BK 1-5).

In one embodiment, the peptidic degradation product is selected from angiotensin I (1-10), angiotensin II (angiotensin 1-8 or Ang 1-8), angiotensin 1-7 (Ang 1-7), and angiotensin 1-5 (Ang 1-5). In an embodiment, the peptidic degradation products that are quantified are angiotensin I (1-10), angiotensin II (angiotensin 1-8 or Ang 1-8), angiotensin 1-7 (Ang 1-7), and angiotensin 1-5 (Ang 1-5).

In another embodiment, the peptidic degradation product is selected from angiotensin II (angiotensin 1-8 or Ang 1-8), angiotensin 1-7 (Ang 1-7), and angiotensin 1-5 (Ang 1-5). In an embodiment, the peptidic degradation products that are quantified are angiotensin II (angiotensin 1-8 or Ang 1-8), angiotensin 1-7 (Ang 1-7), and angiotensin 1-5 (Ang 1-5).

In still another embodiment, the peptidic degradation product is selected from bradykinin 1-9 (BK 1-9), bradykinin 1-8 (BK 1-8), bradykinin 1-7 (BK 1-7) and bradykinin 1-5 (BK 1-5). In an embodiment, the peptidic degradation products that are quantified are bradykinin 1-9 (BK 1-9), bradykinin 1-8 (BK 1-8), bradykinin 1-7 (BK 1-7) and bradykinin 1-5 (BK 1-5).

In still another embodiment, the peptidic degradation product is selected from bradykinin 1-8 (BK 1-8), bradykinin 1-7 (BK 1-7) and bradykinin 1-5 (BK 1-5). In an embodiment, the peptidic degradation products that are quantified are bradykinin 1-8 (BK 1-8), bradykinin 1-7 (BK 1-7) and bradykinin 1-5 (BK 1-5).

The terms "enzyme involved in the proteolytic cascade" or "enzyme of the proteolytic cascade" as used herein shall mean an enzyme which is part of said given proteolytic cascade, forming or degrading at least one peptide involved in the proteolytic cascade. Accordingly, for the RAS proteolytic cascade, enzymes involved in the proteolytic cascade may be selected form renin, aminopeptidases (AP, especially aminopeptidase A (APA) and aminopeptidase N (APN)), dipeptidyl aminopeptidases (DAP), carboxypeptidases (especially ACE2), dipeptidyl carboxypeptidases (especially ACE), and endopeptidases (especially neutral endopeptidase, also called neprilysin). For the bradykinin proteolytic cascade, enzymes involved in the proteolytic cascade may be selected from kallikrein, aminopeptidases (AP, especially aminopeptidase A (APA) and aminopeptidase N (APN)), dipeptidyl aminopeptidases (DAP), carboxypeptidases (especially ACE2), dipeptidyl carboxypeptidases (especially ACE), and endopeptidases (especially neutral endopeptidase, also called neprilysin). The term "actual" as used herein means the actual (or effective)

formation or degradation rate of a peptide, or the actual or effective turnover rate of an enzyme, under the conditions as present in the sample.

The term "equal to" as used herein means that the peptide concentration resulting from any such equal formation or degradation rate(s) of said peptide (the "steady state equilibrium peptide concentration" or "steady state equilibrium peptide level"), or resulting from any such equal turnover rates of at least two enzymes involved in the formation or degradation of said peptide (the "steady state equilibrium enzyme turnover rate"), does not vary more than 15%, 14%, 13%, 12%, 11%, 10%, 9%, 8%, 7%, 6%, 5%, 4%, 3%, 2%, or 1% over a time period of at least 30 minutes (min), 60 minutes, 90 minutes, 120 minutes, 150 minutes, 180 minutes, 210 minutes, 240 minutes, 270 minutes, or 300 minutes. Accordingly, the actual overall turnover rates of the enzymes involved in degradation of said peptide are determined by the actual overall formation rates of their substrate peptide(s), so that any newly or additionally formed substrate is degraded. However, this does not necessarily mean that the net concentration of said peptide is zero, but the net concentration as present in the sample in the steady state equilibrium does not significantly vary as further described above.

Accordingly, in an embodiment of the invention, the concentration of said at least one peptidic degradation product of the proteolytic cascade remains within a constant range over the time period of the steady state equilibrium, despite a continuous flow of formation and degradation. In one embodiment of the invention, the concentration of said at least one peptidic degradation product in steady state equilibrium does not vary more than 15%, 14%, 13%, 12%, 11%, 10%, 9%, 8%, 7%, 6%, 5%, 4%, 3%, 2%, or 1% over a time period of at least 30 minutes, 60 minutes, 90 minutes, 120 minutes, 150 minutes, 180 minutes, 210 minutes, 240 minutes, 270 minutes, or 300 minutes. In one embodiment, the concentration of said at least one peptidic degradation product in steady state equilibrium does not vary more than 15%, or not more than 10%, within 60 minutes. Accordingly, said peptide does neither significantly accumulate nor significantly diminish during the above specified time periods.

In an embodiment, the sample is incubated for up to 15 minutes, 20 minutes, 25 minutes, 30 minutes, 60 minutes, 90 minutes, 120 minutes, 150 minutes, 180 minutes, 210 minutes, 240 minutes, 270 minutes, or up to 300 minutes, before the at least one peptidic degradation product in steady state equilibrium concentration is quantified in the sample. In another embodiment, the sample may be incubated for more than 6 hours (h), especially for up to 8 h, 12 h, 18 h, 24 h or up to 48 h. Suitable incubation time periods mainly dependent on the given proteolytic cascade, on the peptidic analytes to be quantified, on the nature of the sample and on the incubation parameters. Such incubation time periods can easily be determined by a person skilled in the art. In one embodiment, the steady state equilibrium is conserved (or stabilised or frozen or quenched) after incubation. The terms "conserved", "stabilised", "frozen", and "quenched" as used herein shall mean the conservation of a biochemical status, e.g. the conservation of peptide levels, e.g. by inhibition of proteolytic degradation. The stabilisation of the steady state equilibrium peptide levels (or the in vivo peptide levels) can be done by addition of one more protease inhibitors, especially by addition of a protease inhibitor cocktail. Accordingly, one or more protease inhibitors may be added after the incubation until a steady state equilibrium is reached for at least one peptidic degradation product. Suitable protease inhibitors or combinations thereof can be selected by a person skilled in the art and may e.g. comprise a combination of specific or non-specific enzyme inhibitors, or a combination thereof. The one or more protease inhibitors or the protease inhibitor cocktail ensure that especially the proteolytic steps of the cascade which are of interest (i.e. the enzymes forming and degrading the peptides to be measured), or each enzyme of the proteolytic cascade is completely inhibited.

In one embodiment, each step of the proteolytic cascade is inhibited, i.e. each enzyme involved in the proteolytic cascade is inhibited by at least one component of the protease inhibitor cocktail. In another embodiment, the protease inhibitor cocktail comprises at least one specific or non-specific inhibitor of each class of proteases involved in the proteolytic cascade. The protease inhibitor cocktail may comprise one or more inhibitors inhibiting one or more enzymes involved in the proteolytic cascade. Examples for such inhibitors of the RAS are Lisinopril (ACE inhibitor) and Aliskiren (renin inhibitor). The protease inhibitor cocktail may also comprise one or more inhibitors inhibiting one or more groups of enzymes involved in the proteolytic cascade, such as e.g. EDTA (inhibits metalloproteases). Furthermore, the protease inhibitor cocktail may comprise one or more non-specific inhibitors. In one embodiment, the protease inhibitor cocktail comprises a combination of at least two of the aforementioned classes of inhibitors. In another embodiment, the protease inhibitor cocktail comprises one or more inhibitors of the feeding enzyme, especially specific inhibitors of the feeding enzyme.

For example, at least two, at least three, or at least four protease inhibitors are added to the sample. In one embodiment, the protease inhibitor cocktail comprises Pepstatin A, 1,10-Phenanthroline, EDTA, p-Hydroxymercuri-benzoic acid and Z-Arg.

Alternatively, or in addition to the use of one or more protease inhibitors or a protease inhibitor cocktail, the steady state equilibrium may be conserved by the addition of one or more chaotropic agents, such as sodium iodide, sodium perchlorate, lithium perchlorate, magnesium chloride, guanidine thiocyanate (GTC), guanidinium chloride, phenol, propanol, butanol, ethanol, sodium dodecyl sulfate, thiourea, urea or others.

Alternatively, or in addition to the use of one or more protease inhibitors or a protease inhibitor cocktail, the steady state equilibrium may be conserved by other means of physical inactivation of the enzymes in the sample, for example, denaturation of the enzyme induced by heat, salt, pH, or detergent; or by cooling, e.g. placing the samples on ice directly after incubation. For one or more of the further processing steps of the samples, e.g. the plasma or serum separation and the separation by solid phase extraction (SPE; e.g. for matrix depletion and/or peptide enrichment), an according ambient temperature can be selected as well to ensure that all enzymes in the sample are inactive. For example, any sample pre-treatment or sample processing prior to sample analysis may be done at 4° C. ambient temperature (or lower), at least up to the complete denaturation or inactivation of the enzymes involved in the proteolytic cascade (e.g. until eluation from the SPE column).

In contrast, classical PRA assays are aimed on complete inhibition of the degradation pathways of Ang I immediately after the sample has been taken, and the enzyme activity is calculated based on the accumulation rate of the peptide formed by said enzyme. Even if the inhibition of the Ang I degradation pathways may be incomplete in such PRA assays, they are still far from any steady state equilibrium according to the invention, since the net concentration of Ang I significantly changes over time. In the PRA assay as described e.g. in Bystrom et al. (Clin. Chem. 56(2010), 1561-1569), the Ang I concentration significantly increases over time. Moreover, state-of-the-art assays are seeking to assess the overall activity of the RAS by measuring the conformational activated form of renin in plasma samples by ELISA and RIA based methods (DRG Diagnostics, www-.drg-diagnostics.de/49-1-DRG+Renin+active+ELI-SA.html). In contrast to RSSE-Fingerprinting, these assays critically depend on the specificity of the used antibody and allow no conclusions about the concentration of the effector peptides in the samples, which are responsible for the physiologic effects of the RAS. The reason for that is that there exist multiple enzymes affecting the level of effector peptides. All these peptides are simultaneously analysed by RSSE-Fingerprinting while state-of-the-art assays focus on just one enzyme activity or concentration per sample.

In an embodiment of the invention, in the steady state equilibrium, the actual turnover rate of the feeding enzyme is maximal, i.e. the feeding substrate is present in vast molar excess compared to the feeding enzyme, and any addition of external feeding substrate would not further increase the actual turnover rate of the feeding enzyme. Accordingly, the feeding enzyme of a proteolytic cascade is the enzyme, which is responsible for the feeding conversion reaction, i.e. the rate-limiting step of the subsequent proteolytic cascade (or the bottleneck of the proteolytic cascade). For the RAS proteolytic cascade under physiologic conditions, the feeding enzyme is renin, which is responsible for the conversion of angiotensinogen to angiotensin I. In physiological systems (e.g. in the body, in blood, plasma or serum samples), angiotensinogen as the substrate for renin is present in vast molar excess of renin. However, in one embodiment of the invention, one or more, or all other enzymes of the RAS proteolytic cascade, such as e.g. aminopeptidases (especially APA and/or APN), dipeptidyl aminopeptidases, carboxypeptidases (especially ACE2), dipeptidyl carboxypeptidases (especially ACE), and/or endopeptidases (especially neutral endopeptidase, also called neprilysin), are present in the sample at concentrations sufficient to degrade any newly or additionally formed substrate and thus, allow the establishment of a steady state equilibrium for said enzymes and peptide(s) during incubation, i.e. their actual overall turnover rates are determined by the actual overall formation rates of their substrate peptide(s).

According to the present invention, the term "feeding enzyme" shall mean an enzyme with a maximal actual turnover rate, i.e. with an actual turnover rate that is the maximal achievable turnover rate for said enzyme in the sample. The term "maximal achievable turnover rate" shall mean the turnover rate of an enzyme contained in the sample, which can be achieved under the given conditions in the sample, if the substrate peptide is (or would be) present in vast molar excess compared to the enzyme (or a virtually inexhaustible amount) at least until the steady state equilibrium is reached. Accordingly, the actual turnover rate of the feeding enzyme cannot be further increased by the addition of external substrate, since the feeding substrate is already present in vast molar excess compared to the feeding enzyme. If, for example, any external substrate peptide (i.e. a peptide involved in the proteolytic cascade) or an analogue of such substrate is added to a sample before or during the incubation until a steady state equilibrium is reached, this may—according to the definition of the present invention—result in a change of the rate-limiting step(s) for the proteolytic cascade, and thus, also of the feeding enzyme(s) of the proteolytic cascade, if the amount of added substrate peptide is sufficient to result in a maximal achievable turnover rate of at least one enzyme involved in the degradation of said substrate peptide (i.e. an enzyme other than the feeding enzyme under physiologic conditions). For example, if the proteolytic cascade under investigation is the RAS, and if a vast molar excess of an Ang 1-10 (or an analogue thereof, e.g. a Ang 1-10 carrying a mass label or a any covalent modification including amino acid exchanges) compared to one or more or all enzymes involved in Ang 1-10 degradation is added to the sample before or during incubation until a steady state equilibrium is reached, at least one or even all enzymes involved in the degradation of Ang 1-10 (e.g. ACE, ACE2, AP, and/or NEP) would reach maximal achievable turnover rates and thus, would become the rate-limiting feeding step(s) for the subsequent proteolytic reaction(s) of the cascade.

In an embodiment of the invention, feeding enzyme may be added to the sample. The addition of feeding enzyme increases the flow-through of the enzyme cascade and thus, leads to increased absolute levels of peptides, while the relative levels (peptide ratios) remain unchanged. Accordingly, the steady state equilibrium levels of the one or more peptides still reflect the physiological situation, i.e. the enzyme activities, however, the overall peptide levels are increased proportionally. This would be useful, for example, if the peptide levels measured without the addition of feeding enzyme would be below the detection limit of the method used to quantify the peptide(s). Optionally, feeding substrate may be added as well. This may ensure that feeding substrate is and remains in molar excess compared to the feeding enzyme and that feeding substrate is still present in virtually inexhaustible amounts leading to a turnover rate of the feeding enzyme, which is stable for a certain time defining the steady state equilibrium, even if feeding enzyme is added.

In a further embodiment, in the steady state equilibrium the actual overall degradation rate of the product of the feeding enzyme (i.e. the peptide formed by the feeding enzyme) is equal to its actual overall formation rate. In another embodiment, the proteolytic cascade is the RAS, and the product of the feeding enzyme according to the above definition is Ang I. In said embodiment, the actual turnover rate of said Ang I degrading enzyme in the steady state equilibrium is equal to the actual turnover rate of renin, which is the Ang I forming enzyme, if only one enzymatic Ang I degradation pathway is "open" in the sample, i.e. only one Ang I degrading enzyme is active. If more than one Ang I degradation enzymes are active in the sample, the sum of the actual turnover rates of said active Ang I degrading enzymes (i.e. the actual overall degradation rate of Ang I) is equal to the actual turnover rate of renin (i.e. the actual overall Ang I formation rate) in said embodiment.

In another embodiment, in the steady state equilibrium the actual overall degradation rate of more than one peptide, especially of two, three, four, five, six, seven, eight, nine or ten peptides involved in the proteolytic cascade is equal to the actual overall formation rate of said peptide(s). In still another embodiment, in the steady state equilibrium the actual overall degradation rate of each peptide involved in the proteolytic cascade is equal to the actual overall formation rate of said peptides.

Accordingly, a steady state equilibrium is reached for one or more peptide(s) and the related enzyme(s), i.e. the enzyme(s) forming or degrading said peptide(s). As described above, the steady state equilibrium is reached, if the net concentration of the at least one peptide, two or more peptides, or all peptides involved in the proteolytic cascade, does not vary more than 15%, 14%, 13%, 12%, 11%, 10%, 9%, 8%, 7%, 6%, 5%, 4%, 3%, 2%, or 1% over a time period of at least 30 minutes, 60 minutes, 90 minutes, 120 minutes, 150 minutes, 180 minutes, 210 minutes, 240 minutes, 270 minutes, or 300 minutes. Said steady state equilibrium is reached after incubation of the sample for 15 minutes, 20 minutes, 25 minutes, 30 minutes, 60 minutes, 90 minutes, 120 minutes, 150 minutes, 180 minutes, 210 minutes, 240 minutes, 270 minutes, or 300 minutes, or for 8, 12, 18, 24, or 48 h. The steady state equilibrium continues for at least 30 minutes, 60 minutes, 90 minutes, 120 minutes, 150 minutes, 180 minutes, 210 minutes, 240 minutes, 270 minutes, or 300 minutes.

In an embodiment of the invention, in the steady state equilibrium the overall maximal achievable degradation rate of at least one peptide involved in the proteolytic cascade is equal to or higher than its actual overall formation rate. According to the invention, the maximal achievable degradation rate of a peptide is the overall degradation rate which could be achieved under the given conditions in the presence of a vast molar excess of said peptide compared to each enzyme degrading said peptide (or a virtually inexhaustible amount of said peptide), i.e. by addition of external peptide. Accordingly, the maximal achievable degradation rate of a peptide is the sum of maximal achievable turnover rates of all enzymes involved in the degradation of said peptide.

In one embodiment, at the start of the incubation time the amount of all enzymes involved in the proteolytic cascade is in excess of the amount of their respective substrate(s), except for the feeding enzyme of the proteolytic cascade. In another embodiment, the amount of said one or more enzymes or of all enzymes involved in the proteolytic cascade is in excess of the amount of its/their respective substrate(s) during the entire time period of incubation, except for the feeding enzyme of the proteolytic cascade.

In another embodiment, the conditions as specified above (i.e. that the amount of enzyme is in excess of the amount of the respective substrate, and/or that the rate of formation of a peptide is equal to the rate of degradation in steady state equilibrium) apply at least to the one or more peptides to be analysed, and/or the respective enzyme(s) which form or degrade said peptide(s) to be analysed.

For example, if the method of the present invention is used to examine one or more components of the RAS proteolytic cascade, and the peptides to be analysed are, e.g. Ang 1-10 and Ang 1-8, this means that until a steady state equilibrium is reached, the actual rate of formation of Ang 1-10 by renin is higher than the sum of the actual degradation rates of all enzymes involved in Ang 1-10 degradation, including but not limited to ACE, Aminopeptidases and ACE2; and the actual rate of formation of Ang 1-8 by ACE is higher than the sum of the actual degradation rates of all enzymes involved in Ang 1-8 degradation, including but not limited to ACE2, AP, and/or DAP. Accordingly, the Ang 1-10 and Ang 1-8 concentration increases, i.e. Ang 1-10 and Ang 1-8 accumulates, until a steady state equilibrium is reached. When the steady state equilibrium is reached, the actual rate of formation of Ang 1-10 is equal to the sum of the actual turnover rates of all enzymes involved in Ang 1-10 degradation (the actual overall degradation rate of Ang 1-10); and the actual rate of formation of Ang 1-8 is equal to the sum of the actual turnover rates of all enzymes involved in Ang 1-8 degradation (the actual overall degradation rate of Ang 1-8). If, for example, all ten peptides involved in the RAS are to be analysed (as shown, e.g. in FIGS. 2, 3 and 4A, 4C1 and 4C2), the above specified conditions should apply to all ten peptides or to all enzymes involved in the RAS.

Accordingly, in an embodiment of the steady state equilibrium of the present invention, at least one proteolytic degradation reaction has to be active or "open" for at least one, especially for each peptide of the proteolytic cascade to an extent which allows that the actual overall degradation rate is equal to the actual overall formation rate of said peptide, i.e. is not inhibited or "closed", e.g. by use of one or more protease inhibitors, to an extent that the actual overall formation rate exceeds the actual or maximum achievable overall degradation rate of the said peptide.

In one embodiment, chelating agents, such as e.g. EDTA, EGTA, 8-hydroxyquinoline, phenanthroline and dimercaprol (also called British-anti-Lewisite or BAL), are not added before and/or during the incubation until a steady state equilibrium is reached, especially not for the RAS cascade or other proteolytic cascades where metalloproteases are involved, since chelating agents have an inhibitory effect on metalloproteases through chelating of bivalent ions.

In one embodiment, chaotropic agents, such as e.g. sodium iodide, sodium perchlorate, lithium perchlorate, magnesium chloride, guanidine thiocyanate (GTC), guanidinium chloride, phenol, propanol, butanol, ethanol, sodium dodecyl sulfate, thiourea, urea, and/or others, are not added before and/or during the incubation until a steady state equilibrium is reached.

In one embodiment, the steady state equilibrium is reached under physiological conditions for said proteolytic cascade, which means that the components of the proteolytic cascade (enzymes and substrate or product peptides), their total and/or relative amounts as present in the biological sample as taken from the body, as well as the matrix in respect to composition and/or pH of the sample are not or not substantially modified before and/or during the incubation until a steady state equilibrium is reached. In one embodiment, the concentrations of the enzymes and/or peptides involved in the proteolytic cascade present in the biological sample as taken from the body are not modified before and/or during the incubation until a steady state equilibrium is reached.

In another embodiment, substrates or substrate analogues of any enzyme(s) involved in the proteolytic cascade, such as e.g. internal standards or degradation standards, whether in their native form or modified by labelling (e.g. isotopic and/or fluorescent labelling, and/or amino acid modifications or exchanges of at least one amino acid), are not added before and/or during the incubation until a steady state equilibrium is reached. In one embodiment of the present invention, the proteolytic cascade is the RAS, and neither angiotensinogen, angiotensin I and/or angiotensin II, nor any analogues thereof, are added before and/or during the incubation until a steady state equilibrium is reached.

In another embodiment, further substances or reagents, such as e.g. buffer substances (Tris, PBS, MES, HEPES, citrate, borate, carbonate or hydrogen carbonate (or bicarbonate) and/or other buffer substances or respective buffer solutions are not added before and/or during the incubation until a steady state equilibrium is reached.

In still another embodiment, substances or reagents, such as e.g. EDTA, EGTA, PMSF, AEBSF, BSA, maleic acid, maleic anhydride, formic acid, and/or water (in any form, e.g. deionised and/or distilled etc.) are not added before and/or during the incubation until a steady state equilibrium is reached.

However, and not withstanding the foregoing, one or more such aforementioned protease inhibitors, chelating agents, chaotropic agents, substrates, standards, BSA, buffers, and/or other substances or reagents may be added once the steady state equilibrium is reached and optionally quenched.

Especially, one or more standards, e.g. internal standards and/or degradation standards, may be added once a steady state equilibrium is reached and frozen. Standards are, for example, peptides of the proteolytic cascade, which are modified by mass labelling and/or chemical labelling (e.g. isotopic and/or fluorescent labelling, and/or amino acid modifications, and ore the use of mass tags, and/or exchanges of at least one amino acid). Accordingly, internal standards are stable isotope labelled internal standards, e.g. disclosed in WO 03/016861 A.

In one embodiment, the biological sample is incubated as taken from the subject (ex vivo), i.e. the matrix of the sample and/or the concentrations of the components of the proteolytic cascade to be analysed are not modified, but optionally further processed (e.g. to obtain plasma or serum), either before or after a steady state equilibrium is reached and stabilised. Optionally, anti-coagulants, i.e. substances, which prevent coagulation (stopping blood from clotting), may be added to the biological sample before and/or during incubation until a steady state equilibrium is reached. However, such anti-coagulants should not substantially affect the proteases of the proteolytic cascade to be analysed. A suitable anti-coagulant for use in the method according to the present invention is heparin.

If the proteolytic cascade to be analysed is the blood clotting cascade, the skilled person in the art can determine suitable anti-coagulant agents to be added to the sample prior to or during incubation until a steady state equilibrium is reached, which would prevent blood clotting, but would still allow the establishment of a steady state equilibrium for at least one peptide to be analysed. For example, an anti-coagulant could be selected that inhibits blood clotting at a step further downstream in the proteolytic cascade, i.e. not inhibiting any enzyme(s) involved in the degradation of the peptide(s) to be analysed (upstream in the proteolytic cascade).

Prior to analysis, the samples may be pre-treated or further processed, e.g. by plasma or serum separation (e.g. by centrifugation or activation of coagulation followed by centrifugation), and/or purification by solid phase extraction (SPE), e.g. for matrix depletion and/or peptide enrichment. Accordingly, the solid phase extraction may be carried out with a reversed phase chromatography material, a hydrophobic interaction chromatography material, an ion exchange material, affinity chromatography material, e.g. a reversed phase chromatography material, especially a C18, C8 or C6H5 (Phenyl) material.

In one embodiment, the one or more analyte(s) is/are concentrated to dryness after eluting from the solid surface and may be reconstituted in a HPLC compatible solvent, meaning that the composition of the solvent does not interfere with binding of the one or more analytes to the MS coupled HPLC column. The reconstitution solvent is e.g. an aqueous solvent which might be supplemented with additives including propanol, butanol, 2-butanol, pentanol, 2-propanol, acetone, methyl ethyl ketone, acetonitrile, methanol, ethanol, acids or bases in order to enhance solubility of analytes and/or facilitate binding of analytes to the HPLC column.

In another embodiment, the methods according to the invention comprise the steps: providing a sample treated with an anti-coagulant; optionally, further processing the sample to obtain a plasma or serum sample; incubating the sample until a steady state equilibrium is reached for at least one peptidic degradation product involved in the proteolytic cascade; conserving said steady state equilibrium; optionally, adding one or more internal standard(s) once the steady state equilibrium is conserved; conducting a solid phase extraction with the sample; and analysing the sample. The plasma or serum separation may be done either prior to or after the step of incubation until a steady state equilibrium is reached (and optionally stabilised), depending on whether the steady state equilibrium is to be investigated in plasma, serum, or whole blood.

The analysis of the at least one peptidic degradation product in steady state equilibrium concentration may be done e.g. by mass spectrometry (MS); by liquid chromatography, such as high pressure liquid chromatography (also called high performance liquid chromatography, HPLC); especially by liquid chromatography-electrospray ionisation-mass spectrometry (LC-MS), and/or liquid chromatography-tandem mass spectrometry (LC-MS/MS). For example, Cui et al. (Anal Biochem. 369 (2007), 27-33) disclose liquid chromatography-electrospray ionisation-mass spectrometry and liquid chromatography tandem mass spectrometry methods for quantifying angiotensin peptides. For each peptide and corresponding internal standards, different mass transitions can be measured. The performance of the method may be monitored using quality control samples.

Such quality control samples may include, for example, biological samples with pre-defined analyte concentrations, as well as synthetic samples comprising a mixture of pre-defined concentrations of synthetic peptides. For example, the quality control sample may be a pooled blood, plasma, or serum sample or pooled tissue homogenate sample with pre-defined concentrations of one or more peptides. Angiotensin peptide concentrations may be calculated by relating endogenous peptide signals to internal standard signals provided that integrated signals achieved a signal-to-noise ratio above 10.

Furthermore, the analysis may be done by radio immune assay (RIA) or enzyme linked immunosorbent assay (ELISA). Optionally, a HPLC purification step may be done prior to the RIA or ELISA based quantification of peptidic degradation products of the proteolytic cascade.

In one embodiment, the sample pre-treatment, sample processing, and/or the analysis of the samples may be done in a multiwell format, e.g. on 96 well plates.

The present invention provides a novel tool for the analysis of the physiologic or biochemical status of a subject based on the observation of one or more proteolytic cascades in the subject, especially in the blood system of the subject. Especially, the methods of the invention allow the determination of multiple peptide levels under steady state conditions of proteolytic cascades. Moreover, the methods of the invention allow the evaluation of a proteolytic cascade in a compartment specific manner, e.g. the RAS can be analysed in different compartments, such as full blood, serum as well as plasma. The measurement of peptidic degradation products of a proteolytic cascade according to the invention provide a "fingerprint-like" result of the subject's physiologic or biochemical status, or a "fingerprint-like" enzyme activity profile of a subject, which can be indicative for presence or absence of certain diseases or for the effectiveness or ineffectiveness of a treatment of this disease (provided, of course, that the disease directly or indirectly affects the proteolytic cascade). In addition, the methods of the invention allow a comparison of in vivo fingerprints (samples are immediately stabilised and thus, reflect the circulating peptide levels), and ex vivo fingerprints (steady state equilibrium peptide levels in plasma, serum or full blood).

Accordingly, the methods according to the present invention can be used to study a proteolytic cascade in general, its physiologic or biochemical status in a patient or in patient groups, for diagnosing a disease directly or indirectly related to the proteolytic cascade (or the aberrance thereof), to determine a treatment or treatment regime for such disease, to determine fixed dose combinations, to examine the mechanism of action, to minimise drug associated side effects or adverse events, or to examine the pharmacology of drugs in use or of drug candidates, e.g. to examine short term and long term effects or toxicity.

Furthermore, the methods according to the present invention can be used for screening and development of new drugs, biomarkers or biomarker parameters, especially for such screening in the physiologic matrix of said drugs or biomarkers.

In one embodiment, the methods according to the invention are used as a biomarker assay for pathologic conditions or diseases related to the proteolytic cascade(s) under investigation with the methods according to the invention. For example, not only the concentration of one peptidic degradation product, but the entire steady state equilibrium fingerprint (SSE-Fingerprint) comprising several or all peptides involved in the proteolytic cascade under investigation according to the invention, and/or mathematical functions (e.g. products, ratios, sums, differences) of concentrations of two or more peptidic degradation products, and/or combinations of at least two of said mathematical functions, can be used as biomarker (or biomarker compilation).

In another embodiment, the methods according to the invention can be used for determining a specific patient group for a treatment, such as e.g. for the identification of responders and non-responders of a treatment.

The methods according to the present invention can also be used as companion diagnostics. Companion diagnostics are assays (tests or measurements) intended to assist physicians in making treatment decisions for their patients. They do so by providing information on how a drug works in the body and thus elucidating the efficacy and/or safety of a specific drug or class of drugs for single patients, a targeted patient group or sub-groups. There are two main groups of companion diagnostics that include tests that are used for drugs that are already on the market as well as tests that are already used in the preclinical or clinical development phase of a potential drug. The use of companion diagnostics for drugs already in early development has the potential to significantly alter the drug development process and commercialisation of drug candidates by yielding safer drugs with less side effects, with enhanced therapeutic efficacy in a faster, more cost-effective manner.

Accordingly, the subject from which the biological sample is taken may have been treated with one or more pharmaceutical compositions (in vivo), e.g. a pharmaceutical composition comprising a protease inhibitor, especially, if the method according to the present invention is used to monitor the effects of a pharmaceutical composition, or to determine the optimal dose of a pharmaceutical composition, or to assess any potential toxic interactions of one or more pharmaceutical compositions, or to examine multiple drug interactions.

In an embodiment of the invention, the subject is a human. In another embodiment, the subject is an animal, for example a mammalian, a rodent, a pig, or a monkey.

The method according to the present invention is a standardised procedure for the overall assessment of a proteolytic cascade in blood samples but is also suited for proteolytic cascades in other samples, especially tissue biopsies, tissue homogenates, tissue slices, liquor, bile fluid, urine, etc. The present invention can be used in principle for all proteolytic cascades (under the control of enzymatic cleavage of proteins or peptides into peptidic degradation products being either metabolites or intermediates or end products of a proteolytic cascade), which occur in the blood system. The present invention is specifically suited for the most relevant proteolytic cascades in the human blood system, such as the RAS, the blood-clotting cascade, the complement system, apoptosis pathways, neuropeptide cascades, endothelin peptide cascades, natriuretic peptide cascades. With the present invention, a method for the measurement of steady state equilibrium peptide concentrations, which reflect the activity and conversion rates of their metabolising enzymes, is provided. A steady state equilibrium concentration of a peptide in that context means that its rate of formation is equal to its rate of degradation leading to a peptide concentration, which does not substantially or significantly change over time for a certain period of time, and which is strongly dependent on affinities of the enzymes to their substrates under the given conditions rather than maximal enzyme conversion rates, as further described above. Since the present invention deals with biological systems, it is clear that the term "steady state equilibrium" cannot be regarded as a single point to be reached, but more as a kinetic target region of peptide concentrations, which do not significantly change over time for a certain period of time. More accurate time periods until such steady state equilibrium concentrations are reached are mainly dependent on the given proteolytic cascade, on the peptidic analytes to be quantified, on the nature of the sample and on the incubation parameters. This can easily be determined for each cascade. In general, the "steady state equilibrium window" wherein the quantification according to the present invention can be performed is rather large, at least for some of the proteolytic cascades, especially those in blood. Usually, the steady state equilibrium is reached after a certain incubation time, which is empirically determined (e.g. 30 minutes for the RAS system) and then stays stable for an extended period of time (e.g. 6 hours (h) for the RAS system). Then, the steady state equilibrium is disturbed by effects such as degradation and inactivation of the involved enzymes or a lack of feeding substrate in the sample. The feeding substrate concentration based time of stability ($t_s$) for a given cascade can be calculated by dividing the concentration of the feeding substrate (or feeding precursor peptide) ($c_f$) reduced by an enzyme- and sample-specific constant defining the minimal substrate concentration to achieve the maximal turnover rate of the feeding enzyme in the sample ($c_{min}$), by the turnover rate of the feeding enzyme of the cascade, thereby defining the feed rate ($V_f$) of the cascade.

$$t_s = (c_f - c_{min})/V_f$$

$t_s$ feeding substrate concentration based time of stability [h]
$c_f$ feeding substrate concentration [mol/L]
$c_{min}$ sample specific minimal substrate concentration to achieve the maximal turnover rate of the feeding enzyme in the sample [mol/L]
$V_f$ feed rate of the cascade [[mol/L]/[h]]
and $$c_{min} = f \cdot c_E$$

f excess factor
$c_E$ feeding enzyme concentration

For example, the application of these formulas above on the RAS, where the feeding conversion is carried out by renin, yields a calculated feeding substrate concentration based time of stability of the RAS steady state equilibrium of about 60 to 200 hours based on different published values for PRA (plasma renin activity, PRC (plasma renin concentration), see e.g. [Nishiyama et al. 2010, and Bystrom et al., Clin. Chem. 56(2010), 1561-1569], and applying a AGT concentration of e.g. 70 µg/ml plasma and an excess factor of e.g. 1000. Of course, said calculated feeding substrate concentration based time of stability should serve as a rough and theoretic reference point only, since the actual time of stability of the steady state equilibrium may differ significantly in the samples.

The method according to the present invention is specifically suited for the monitoring and analysis of Ang 1-10 and its degradation products, thereby observing the status of the RAS in human blood samples. The steady state equilibrium concentrations of Ang 1-10 and its degradation products are highly indicative of the physiologic or biochemical status of the subject. For example, deviations from normal distribution of the Ang 1-10 degradation products are indicative for enzymatic malfunction of the RAS and/or the bradykinin system, which can lead to e.g. a pathologic increase in blood pressure or other pathologic conditions or diseases. On the other hand, from the distribution and relative concentrations of the Ang 1-10 degradation products in the steady state equilibrium according to the present invention type and effectiveness of therapeutic treatments targeting the RAS can be monitored. Surprisingly, the steady state equilibrium concentrations according to the present invention provide much better indications and correlations than the determination of Ang 1-10 or other degradation products in blood samples without allowing them to reach the steady state equilibrium (i.e. the "classical" blood samples immediately stabilised).

In contrast to state-of-the-art methods, where inhibitors are used to immediately stabilise peptides produced by certain enzymes with limited success [Bystrom et al., Clin. Chem. 56(2010), 1561-1569], according to the present invention the sample is allowed to reach an enzyme activity defined steady state equilibrium for at least one peptide involved in the proteolytic cascade. This innovative approach allows a highly reproducible overall assessment of the proteolytic cascade, especially RAS, in the physiological sample matrix while integrating all enzyme activities involved in the metabolism of the peptides of the proteolytic cascade. Another advantage over state-of-the-art technologies is that substrate concentrations in the assay according to the present invention generally remain below the concentration of metabolising enzymes (except for the feeding enzyme), taking into consideration the affinity of the enzyme for each single substrate under the given conditions in the sample (e.g. physiologic conditions) in contrast to in vitro enzyme activity assays, where this important feature is neglected for means of simplification by using excess amounts of substrate.

Finally, the measurement of steady state equilibrium peptide levels by the method according to the present invention allows the identification of potential sites of de-regulation in patient samples, paving the way for a patient specific approach in the therapeutic manipulation of the proteolytic cascades affected by the patient's disease (e.g. selection of the type of RAS targeted medication in the treatment of hypertension and prediction of drug resistances) and bearing significant potential for the use of the method in the discovery of biomarkers.

The present invention therefore provides an excellent ex-vivo platform for diagnostic analyses, especially for the diagnosis of a disease related to a proteolytic cascade, especially the RAS. Such disease related to the RAS includes, for example, hypertension, cardiac diseases, especially congestive heart failure, chronic heart failure, acute heart failure, arteriosclerosis, myocardial infarction, kidney diseases, especially renal failure, diabetic nephropathy, lung diseases, especially acute lung injury and/or acute respiratory distress syndrome (ARDS), liver diseases, especially fibrosis, inflammatory diseases, especially sepsis, arthritis, rheumatitis, and/or cancer. The invention is also suited for large-number routine analysis of patients, for e.g. identifying RAS affecting substances, assessing the effects of RAS affecting substances, and/or monitoring patients being under RAS affecting medication. Such RAS affecting medication may include one or more active ingredients such as, for example, aminopeptidase inhibitors, especially amastatin; ACE inhibitors, especially captopril, enalapril, fosinopril, lisinopril, perindopril, quinapril, ramipril, trandolapril, benazepril; angiotensin II receptor antagonists, especially candesartan, eprosartan, irbesartan, losartan, olmesartan, telmisartan, valsartan; aldosterone receptor antagonists, especially eplerenone, spironolactone; and/or ACE2, especially recombinant soluble human ACE2 and renin inhibitors, especially aliskiren.

Specifically for blood samples, it is important for reaching the steady state equilibrium for at least one peptide involved in the proteolytic cascade, that the proteases of the proteolytic cascade to be observed with the present method are not inhibited by addition of protease inhibitors to the sample, at least not to an extend which does not allow at least one enzyme involved in the degradation of said at least one peptide to work until the steady state is reached for said at least one peptide, i.e. at least one degradation enzyme of said peptide(s) has to be active to an extend to allow steady state equilibrium for said peptide(s). Therefore, in one embodiment, protease inhibitors are not added to the sample to an extent, that the activities of the proteases involved in the formation and degradation of the at least one peptide to be analysed are significantly inhibited, before and/or during the incubation until a steady state equilibrium is reached. According to said embodiment, the samples are not combined with such protease inhibitors or, if such inhibitors have already been added, such inhibitors are inhibited (in their protease inhibiting function) or removed before and/or during the incubation until a steady state equilibrium is reached. Of course, inhibitors which do not affect the proteases of the relevant proteolytic cascade which should be studied by the method according to the present invention, but which inhibit other proteolytic activities (e.g. inhibitors of blood coagulation if the RAS is studied), can be added to the sample, because this would not affect the ability of the relevant proteolytic cascade (i.e. the cascade to be analysed, e.g. the RAS) to reach a steady state equilibrium for at least one peptide of the cascade.

Proteolytic cascades are present in a high number of physiological processes from the simple digestion of proteins (e.g. food protein or proteins to be eliminated from body cells or body fluids) to highly regulated cascades, such as the RAS or the blood coagulation system. Proteases can either break specific peptide bonds (limited proteolysis), depending on the amino acid sequence of a protein, or break down a complete peptide to amino acids (unlimited proteolysis). The specific cleavage of peptide bonds is a central mechanism for regulation of complex biological processes. Especially peptide hormones are frequently produced as inactive precursor peptides, which are present in circulation in excessive amounts. Selective proteases are necessary to liberate the active hormones, which are then in turn degraded by other proteases.

In one embodiment, the type of sample, which can be analysed according to the present invention, is a blood sample. "Blood sample" according to the present invention can be any sample containing blood or one or more of its fractions (containing the proteases of the relevant proteolytic cascade). Specifically, all blood samples, which are routinely provided from human donors can be used according to the present invention, i.e. full blood, plasma or serum, especially fresh or frozen anti-coagulated full blood or fresh or frozen anti-coagulated plasma. "Anti-coagulated" blood or plasma contains anti-coagulants, i.e. substances, which prevent coagulation (stopping blood from clotting), of course, without affecting the proteases of the proteolytic cascade to be analysed in their ability to reach a steady state equilibrium. A suitable anti-coagulant is heparin; heparinised blood samples are therefore a suitable source material for the method according to the present invention. Heparinised blood samples may be further processed before the method according to the present invention is applied. For example, heparinised plasma or serum may be derived from the blood sample. Alternatively, the method according to the present invention may also be performed on full blood, i.e. with all blood cells still being present (as well as the proteases on or in such cells). More generally acting protease inhibitors as anti-coagulants, such as citrate or EDTA are less suitable; or, in the alternative (if the sample e.g. already contains such anti-coagulants) may require the addition of neutralising substances for such protease inhibitors in order to allow incubation of the sample until a steady state equilibrium is reached.

With the method according to the present invention, not only one specific peptide or peptidic degradation product as a marker for the status of a proteolytic cascade can be identified. It is possible to analyse more than one of the peptide members of the cascade, thereby allowing an even further fine-tuned analysis of the physiologic or biochemical status of this cascade in the subject. It has turned out in the course of the present invention that the relative amounts of different peptide members of a proteolytic cascade in the steady state equilibrium are highly indicative of the physiologic or biochemical status of this cascade in the subject. For example, the ratio of molar amounts or concentrations of two or more proteolytic degradation products in steady state equilibrium can be indicative of an enzyme activity, a related physiologic condition or pathology. An example provided with the present invention is the molar ratio of Ang 1-8 to Ang 1-10 (or relative ratios of other Ang 1-10 degradation products) in steady state equilibrium, which is indicative of the RAS status of the subject and/or the RAS influencing treatment regime applied to the subject (e.g. treatment with substances like Lisinopril, Amastatin, ACE, ACE2, NEP, etc.).

Therefore, one embodiment of the present invention comprises the quantification of at least two, at least three, especially at least four peptidic degradation products of the proteolytic cascade in the sample in steady state equilibrium concentration. With the methods of the present invention, it is possible to quantify as many degradation products in the proteolytic cascade in steady state equilibrium as possible (or: as known) to get a "fingerprint-like" assessment of the status of the proteolytic cascade.

According to the present invention it is necessary to quantify the one or more proteolytic degradation products in the steady state equilibrium. This is essentially different from prior art analyses, which usually apply quantification of analytes in a status of the proteolytic cascade immediately stabilised after the samples (i.e. blood samples) are taken from the subjects, i.e. not in a steady state equilibrium. Usually, such prior art samples have been treated with protease inhibitors immediately after taking of the samples in order to inhibit unwanted enzyme dependent changes in the cascade. The present invention, however, uses such enzyme dependent changes in analysing the physiologic or biochemical status of the subject concerning the proteolytic cascade by specifically allowing the proteases of said cascade under investigation to perform their proteolytic activity until a steady state equilibrium is reached. This will usually lead to a change in the amount and composition of the peptidic degradation products in the proteolytic cascade under investigation compared to the sample immediately stabilised after the taking of the sample from the subject. According to the invention, the sample specific proteolytic activity leads to a steady state equilibrium which is much more indicative of the biochemical status of the subject concerning this cascade than the immediately stabilised sample (without the incubation step until a steady state equilibrium is reached according to the present invention).

As already indicated above, the steady state equilibrium according to the present invention is not a single, quantitatively exactly determined and isolated point, but a status where changes in the relative ratios have been substantially reduced in the sample. Usually, such a steady state equilibrium can be reached by applying usual incubation conditions for the given samples and the cascade under investigation. As specified above, the sample may be incubated for up to 15 minutes, 20 minutes, 25 minutes, 30 minutes, 60 minutes, 90 minutes, 120 minutes, 150 minutes, 180 minutes, 210 minutes, 240 minutes, 270 minutes, or 300 minutes. For the RAS and/or the bradykinin system, the samples may be incubated for at least 30 min to up to 300 min, or for at least 30 min to up to 180 min, or for at least 30 min to up to 120 min, or for at least 30 min to up to 90 min, or for at least 30 min to up to 60 min. Suitable incubation temperatures are those present in the physiologic system or those, wherein the proteases of the proteolytic cascade under investigation have their optimal temperature of action, e.g. at a temperature of 30 to 50° C., 35 to 40° C., or especially of about 37° C. (specifically for human blood samples).

As already stated, the present invention is further exemplified in the example section, especially on the renin-angiotensin-system (RAS) and the bradykinin system. The one or more peptidic degradation products to be analysed can be selected from angiotensin peptides, such as angiotensin I (Ang 1-10), angiotensin 2-10 (Ang 2-10), angiotensin II (angiotensin 1-8 or Ang 1-8), angiotensin III (angiotensin 2-8 or Ang 2-8), angiotensin IV (angiotensin 3-8 or Ang 3-8), angiotensin 1-9 (Ang 1-9), angiotensin 1-7 (Ang 1-7), angiotensin 2-7 (Ang 2-7), angiotensin 3-7 (Ang 3-7) and angiotensin 1-5 (Ang 1-5); and/or from kinin peptides, such as kallidin (KD or Lys-bradykinin) and its biological degradation products, such as bradykinin 1-9 (BK 1-9), bradykinin 2-9 (BK 2-9), bradykinin 1-8 (BK 1-8), bradykinin 1-7 (BK 1-7) and bradykinin 1-5 (BK 1-5).

In an embodiment, the peptidic degradation product is selected from angiotensin I (1-10), angiotensin II (angiotensin 1-8 or Ang 1-8), angiotensin 1-7 (Ang 1-7), and angiotensin 1-5 (Ang 1-5). In another embodiment, the peptidic degradation product is selected from angiotensin II (angiotensin 1-8 or Ang 1-8), angiotensin 1-7 (Ang 1-7), and angiotensin 1-5 (Ang 1-5). In still another embodiment, the peptidic degradation product is selected from bradykinin 1-9 (BK 1-9), bradykinin 1-8 (BK 1-8), bradykinin 1-7 (BK 1-7) and bradykinin 1-5 (BK 1-5).

Since the method according to the present invention applies the proteolytic activities contained in the sample, the one or more samples, especially blood samples, should be free of added protease inhibitors for the proteolytic cascade before the steady state equilibrium is reached.

Such protease inhibitors may be added after the incubation until a steady state equilibrium is reached and stabilised. This safeguards that the peptide concentrations reflecting the steady state equilibrium are still present during the quantification step (although the steady state equilibrium is usually stable over a certain period of time, this provides additional quality assurance for the method according to the present invention).

With the methods according to the present inventions it is possible to monitor the status of the RAS and/or the bradykinin system. In one embodiment, at least two peptidic degradation products are quantified and a ratio is calculated of the steady state equilibrium quantifications of the at least two peptidic degradation products. Accordingly, one embodiment of the present invention employs the quantification of at least two of angiotensin I (Ang 1-10), angiotensin 2-10 (Ang 2-10), angiotensin II (angiotensin 1-8 or Ang 1-8), angiotensin III (angiotensin 2-8 or Ang 2-8), angiotensin IV (angiotensin 3-8 or Ang 3-8), angiotensin 1-9 (Ang 1-9), angiotensin 1-7 (Ang 1-7), angiotensin 2-7 (Ang 2-7), angiotensin 3-7 (Ang 3-7) and angiotensin 1-5 (Ang 1-5), kallidin (KD or Lys-bradykinin) and its biological degradation products, such as bradykinin 1-9 (BK 1-9), bradykinin 2-9 (BK 2-9), bradykinin 1-8 (BK 1-8), bradykinin 1-7 (BK 1-7) and bradykinin 1-5 (BK 1-5). Then, a ratio or product of those at least two peptidic degradation products may be calculated to provide an especially indicative parameter for the status of the proteolytic cascade, e.g. the RAS, in the sample. For example, the steady state equilibrium concentration ratio between Ang 1-8 and Ang 1-10 is indicative of the physiologic or biochemical status, function, and/or activity of ACE. Accordingly, the ratio between a peptidic degradation product and its precursor peptide (i.e. the substrate of the enzyme forming said peptidic degradation product) in steady state equilibrium is indicative of the physiologic or biochemical status, function, and/or activity of the enzyme which cleaves said substrate into said peptidic degradation product. In an embodiment, more than one ratio between a peptidic degradation product and its precursor peptide are calculated. Said at least two ratios may be again related to each other, e.g. by calculating the ratio or product of the at least two ratios, or by addition or subtraction of ratios, or both (calculating the ratio(s) between sums and/or differences or subtractions). In another embodiment, the ratio between at least one in vivo peptide level (immediately stabilised) and the same peptide level in steady state equilibrium is calculated.

The method according to the present invention is dependent on an exact and accurate quantification of the peptidic degradation products. Since many samples, especially blood samples contain proteins, salts, acids, bases, lipids, phospholipids or other components, which can disturb peptide quantification; methods for pre-treatment of the samples before quantification may be applied.

The method according to the invention may be conducted by using a kit.

Accordingly, in another aspect, the present invention concerns a kit for the measurement of peptidic degradation products of a proteolytic cascade in a biological sample in steady state equilibrium concentration. The kit may comprise an instruction to incubate the sample for a certain time period until a steady state equilibrium is reached for at least one peptidic degradation product of the proteolytic cascade. The kit may further comprise one or more instructions for conducting the method according to the present invention, as specified above.

Accordingly, in one embodiment, the kit for the measurement of peptidic degradation products of a proteolytic cascade in a biological sample in steady state equilibrium concentration (i.e. a kit for conducting the method according to the invention) comprises an instruction to incubate the one or more samples for a certain time period until a steady state equilibrium is reached for at least one peptidic degradation product of the catalytic cascade. Optionally, the kit further comprises one or more chemical, biochemical and/or biotechnological reagents selected from peptides, enzymes, enzyme inhibitors, buffers, solvents, chaotropic agents, detergents, and combinations thereof. Optionally, the kit further comprises one or more chemical, biochemical and/or biotechnological laboratory items selected from solid phase extraction materials or other purification materials, containers, and combinations thereof. Optionally, the kit further comprises one or more biological samples selected from blood samples, serum samples, plasma samples, tissue samples, and combinations thereof. For example, said biological samples can be blood, serum, plasma and/or tissue samples and may be used e.g. as a standard and/or quality control. Said containers can be tubes or sample collection vials, or any other standard container suitable to comprise chemical, clinical, biochemical and/or biotechnological material. In an embodiment, the container is a blood or tissue container. Said container optionally comprises one or more anti-coagulants, such as e.g. heparin, EDTA, and/or other anti-coagulants. Said container may further comprise one or more enzyme inhibitors or a protease inhibitor cocktail, such as further specified above or in the example section.

In an embodiment, the kit further comprises one or more protease inhibitors or inhibitor cocktails, one or more feeding substrates, one or more blood collection tubes, optionally coated with heparin, one or more standards, one or more quality control samples, one or more solid phase extraction materials, and/or one or more solvents, or combinations thereof.

The components of the kit and the instructions comprised by the kit are further defined above with regard to the methods of the present invention. The instruction to incubate the samples for a certain time period until a steady state equilibrium is reached for at least one peptidic degradation product or a catalytic cascade may, for example, include information about the methods, reagents, and/or conditions as specified above with regard to the methods of the present invention, for example, information as to the duration and conditions for incubation, sample stabilisation, and/or analysis. Accordingly, the instruction may include further instructions, such as e.g. not to add any protease inhibitors prior to and/or during incubation until a steady state equilibrium is reached, and/or to inactivate or remove any protease inhibitor which may have been added. Specific applications like the measurement of single protease activities based on steady state peptide measurements or the influence of certain protease inhibitors (or respective pharmaceutical compositions) on the proteolytic cascade and peptide levels in steady state equilibrium might require the addition of certain protease inhibitors before the incubation to reach steady state equilibrium. Thus, the instructions may include instructions to add certain protease inhibitors. However, as specified above, at least one proteolytic degradation reaction has to be active for at least one peptide of the proteolytic cascade to an extent which allows that the actual overall degradation rate is equal to the actual overall formation rate of said peptide.

Such instruction may be provided, for example, in a paper format (e.g. as a leaflet or manual) or electronically. Such instruction may directly or indirectly accompany the kit, e.g. it is provided by the manufacturer and/or supplier of the kit and comprised by the kit package or provided otherwise together with the kit (e.g. by email from the manufacturer and/or supplier of the kit or by download from a web page of the manufacturer and/or supplier of the kit).

In another aspect, the present invention relates to the use of the kit for the measurement of peptidic degradation products of a proteolytic cascade in a biological sample in steady state equilibrium concentration. Such use of the kit is further specified above with regard to the methods according to the invention. In an embodiment, the use of the kit comprises the step of incubating the sample until a steady state equilibrium is reached for at least one peptidic degradation product involved in said proteolytic cascade. In another embodiment, the use of the kit comprises the step of quantifying said at least one peptidic degradation product in a steady state equilibrium concentration in the sample.

According to another aspect, the present invention concerns a physical or electronic representation of the result of quantification of the method according to the present invention or of the use of the kit according to the present invention, wherein at least two peptidic degradation products have been quantified on a physical or electronic carrier and wherein the quantified amounts of the at least two degradation products are provided in the sequence of the proteolytic cascade. In other embodiments, at least three or at least four peptidic degradation products have been quantified on a physical or electronic carrier and the quantified amounts of the at least three or four degradation products are provided in the sequence of the proteolytic cascade.

In one embodiment of the physical or electronic representation according to the present invention, the results of quantification of at least two or at least three of angiotensin I (Ang 1-10), angiotensin 2-10 (Ang 2-10), angiotensin II (angiotensin 1-8 or Ang 1-8), angiotensin III (angiotensin 2-8 or Ang 2-8), angiotensin IV (angiotensin 3-8 or Ang 3-8), angiotensin 1-9 (Ang 1-9), angiotensin 1-7 (Ang 1-7), angiotensin 2-7 (Ang 2-7), angiotensin 3-7 (Ang 3-7) and angiotensin 1-5 (Ang 1-5), kallidin (KD or Lys-bradykinin) and its biological degradation products, such as bradykinin 1-9 (BK 1-9), bradykinin 2-9 (BK 2-9), bradykinin 1-8 (BK 1-8), bradykinin 1-7 (BK 1-7) and bradykinin 1-5 (BK 1-5) are included and provided in dependence of their relative quantities.

Accordingly, this physical or electronic representation may be provided in a form, wherein the results of quantification of angiotensin I (Ang 1-10), angiotensin 2-10 (Ang 2-10), angiotensin II (angiotensin 1-8 or Ang 1-8), angiotensin III (angiotensin 2-8 or Ang 2-8), angiotensin IV (angiotensin 3-8 or Ang 3-8), angiotensin 1-9 (Ang 1-9), angiotensin 1-7 (Ang 1-7), angiotensin 2-7 (Ang 2-7), angiotensin 3-7 (Ang 3-7) and angiotensin 1-5 (Ang 1-5) are included and provided in dependence of their relative quantities. According to another embodiment, this physical or electronic representation may be provided in a form, wherein the results of quantification of kallidin (KD or Lys-bradykinin) and its biological degradation products, such as bradykinin 1-9 (BK 1-9), bradykinin 2-9 (BK 2-9), bradykinin 1-8 (BK 1-8), bradykinin 1-7 (BK 1-7) and bradykinin 1-5 (BK 1-5) are included and provided in dependence of their relative quantities.

In one embodiment, this physical or electronic representation may be provided in a form, wherein the results of quantification of angiotensin I (1-10), angiotensin II (angiotensin 1-8 or Ang 1-8), angiotensin 1-7 (Ang 1-7), and angiotensin 1-5 (Ang 1-5) are included and provided in dependence of their relative quantities.

In another embodiment, this physical or electronic representation may be provided in a form, wherein the results of quantification of angiotensin II (angiotensin 1-8 or Ang 1-8), angiotensin 1-7 (Ang 1-7), and angiotensin 1-5 (Ang 1-5) are included and provided in dependence of their relative quantities.

In still another embodiment, this physical or electronic representation may be provided in a form, wherein the results of quantification of bradykinin 1-9 (BK 1-9), bradykinin 1-8 (BK 1-8), bradykinin 1-7 (BK 1-7) and bradykinin 1-5 (BK 1-5) are included and provided in dependence of their relative quantities.

In still another embodiment, this physical or electronic representation may be provided in a form, wherein the results of quantification of bradykinin 1-8 (BK 1-8), bradykinin 1-7 (BK 1-7) and bradykinin 1-5 (BK 1-5) are included and provided in dependence of their relative quantities.

This physical or electronic representation of the peptidic degradation products according to the present invention is a valuable diagnostic tool for any physician allowing a significant assistance in the diagnosis of a disorder or disease (e.g. a disorder or disease connected to the RAS). It allows comparison between healthy and diseased status (or the comparison of different stages of the disease or different stages in the treatment) in a "fingerprint-like" manner, i.e. by a multi-parameter representation of the quantification results obtained (as shown in the graphic representations in the figures according to the present invention ("RAS-Fingerprints")). These results can be provided electronically. In the electronic format, comparison and development of these patterns over time either from the same patient, or over a population or patient group, can easily be analysed and monitored. In graphic representations, the proteolytic cascade can be depicted so that the results of the present method are not only quantification results, but also complex and interdependent "fingerprint-like" results being of high value in the diagnosis of a disease and/or treatment depicting the biochemical relations underlying the peptide concentrations. This tool according to the present invention therefore allows an improved use of the results obtained with the method according to the present invention.

The invention is further described by the following examples and the figures, of course without being limited thereto:

FIG. 1 shows the RAS steady state equilibrium (RSSE). (A) Heparin blood was collected from a healthy donor and incubated at 37° C. After indicated time periods protease inhibitor cocktail was added to an aliquot of the heparinised blood sample to conserve the steady state equilibrium. Concentrations of angiotensin 1-10 (blue) and angiotensin 1-8 (green) are shown and compared with an aliquot of the blood sample collected from the same donor, which was stabilised immediately during collection (ICE, t=0). (B) Steady state equilibrium angiotensin concentrations in heparinised blood were determined in the absence (red; control) and presence of indicated RAS inhibitors (blue). The steady state equilibrium was frozen by adding a protease inhibitor cocktail to the samples immediately (0 h) or after 2 h and 4 h of incubation at 37° C. (C) Angiotensin concentrations in heparinised blood were determined in the absence (red; control) and presence of EDTA and AEBSF (blue). The incubations were frozen by adding a protease inhibitor cocktail to the samples immediately (0 h) or after 2 h and 4 h of incubation at 37° C. Concentrations of angiotensin 1-10 and angiotensin 1-8 are shown.

FIG. 2 shows the pharmacologic manipulation of the RAS steady state equilibrium. Indicated agents were added prior to an incubation period of 2 h followed by LC-MS/MS based RSSE-Fingerprinting. Results are shown in fingerprint illustrations displaying angiotensin peptide concentrations as differently sized spheres and metabolising enzymes represented by blue arrows and letters. Annotations beneath the spheres are constituted by peptide name and peptide concentration in pg/ml blood. RSSE-Fingerprints are shown for low-molecular-weight RAS inhibitors (A), exogenously added RAS enzymes (B) and combinations of both (C).

FIG. 3 shows matrix dependence of RSSE-Fingerprinting. Heparinised blood, plasma and plasma subjected to one freeze/thaw cycle were prepared from the same donor and subjected to RSSE-Fingerprinting performing a 2 h-37° C. incubation followed by conserving the steady state equilibrium adding a protease inhibitor cocktail to the samples and LC-MS/MS analysis. Fingerprint graphs of control samples without pharmacologic manipulation (A) are given and compared with samples where Amastatin (B) or ACE2 in combination with Lisinopril (C) where added before the incubation period.

FIG. 4 shows RAS—as well as RSSE-Fingerprinting in healthy volunteers. Blood samples were collected from healthy volunteers in the presence of protease inhibitor cocktail to conserve angiotensin peptide levels as present in vivo, i.e. prior to any equilibration (RAS-Fingerprint or in vivo RAS-Fingerprint) and compared to heparinised blood and plasma subjected to incubation until a steady state equilibrium is reached (RSSE-Fingerprint or ex vivo Fingerprint) in parallel. The mean RAS-Fingerprint (conserved in vivo peptide levels) and the mean RSSE-Fingerprints (conserved ex vivo generated steady state equilibrium peptide levels) for heparin blood and plasma for 12 healthy volunteers are shown (A). The molar SSE-Ratio for ACE [fmol/ml Ang 1-8]/[fmol/ml Ang 1-10] was calculated and presented in the together with corresponding angiotensin 1-10 and angiotensin 1-8 concentrations in pg/ml and fmol/ml for each subject donor (B). The tables show the values for peptide levels constituting the RAS-Fingerprints (FIG. 4B1; Table 1), RSSE-Fingerprints from Blood (FIG. 4B2; Table 2) and RSSE-Fingerprints from plasma (FIG. 4B3; Table 3) for all donors as well as calculated MEAN and SEM. The RAS- and RSSE-Fingerprints of 2 out of the 12 healthy donors are shown together with corresponding values for molar SSE-Ratios below (C; 4C1: Donor 3, 4C2: Donor 6).

FIG. 5 shows an overview of the main peptide degradation steps of the bradykinin system, i.e. the main bradykinin peptides and the respective enzymes forming and/or degrading those peptides.

FIG. 6 shows the tables with the peptide levels measured for the RAS (A) and the bradykinin system (B) in the same plasma samples, stabilised with GTC after incubation for the indicated time periods.

EXAMPLES

Materials:
C18 Cartridges: SEP-PAK™ Vac 3 cc (500 mg), Waters
Mass Spectrometer: Q TRAP4000—Applied Biosystems
HPLC System: 1100 Series, Agilent
C18 RP-HPLC column: Luna 3u C18(2) 100A, 100×2.00 mm, (Phenomenex, Cat. no. 00D-4251-B0)
Reagents:
Ethanol, abs. (Merck, Cat. no. 100983)
Methanol, (Fluka, Cat. no. 14262)
Water, LiChrosolv (Merck, Cat. no. 115333)
Acetonitril, LiChrosolv (Merck, Cat. no. 114291)
Formic acid, >98%, (Fluka, Cat. no. 06440)
Z-Arg, as Renin inhibitor, (Bachem, C-3195)
Pepstatin A (Bachem N-1125)
p-Hydroxymercuribenzoic acid, sodium salt (Fluka, 55540)
1,10-Phenanthroline monohydrate (Sigma, P9375)
Lisinopril (Sigma, L6394)
Captopril (Sigma, C4043)
Amastatin.HCl, (Bachem, N-1410)
ACE, NEP and APN were purchased from R&D Systems.
rhACE2 (recombinant soluble human ACE2) was produced by Apeiron Biologics.
EDTA (Sigma)
GTC (Sigma, Cat. no. G9277)
Trifluoroacetic acid (TFA) (Sigma-Aldrich, Cat. no. 302031)
Internal Standards:

The internal standards used for absolute quantification of peptides in biological samples were synthetic peptides, their sequence was identical to the peptides analytes and was tagged with a mass label allowing the discrimination between endogenous peptides and standard peptides in LC-MS/MS analysis. The identical physicochemical properties of these synthetic peptides make them ideal internal standards for low abundance peptide quantification showing identical behaviour and recovery during sample processing compared to their corresponding peptide analyte. The internal standards were subjected to the sample during or directly after blood collection, taking into consideration all manipulation induced variations. The use of peptide specific internal standards is recommendable, as peptide recoveries may differ between different peptides and individual samples.

Furthermore, the MS/MS-fragmentation characteristics of endogenous and standard peptides are identical allowing high accuracy and precision in determining absolute peptide levels.

Example I: Analysis of Proteolytic Cascade Degradation Products in Blood Samples According to the Present Invention (RSSE Fingerprint)

RSSE-Fingerprinting.

Figure 3A:
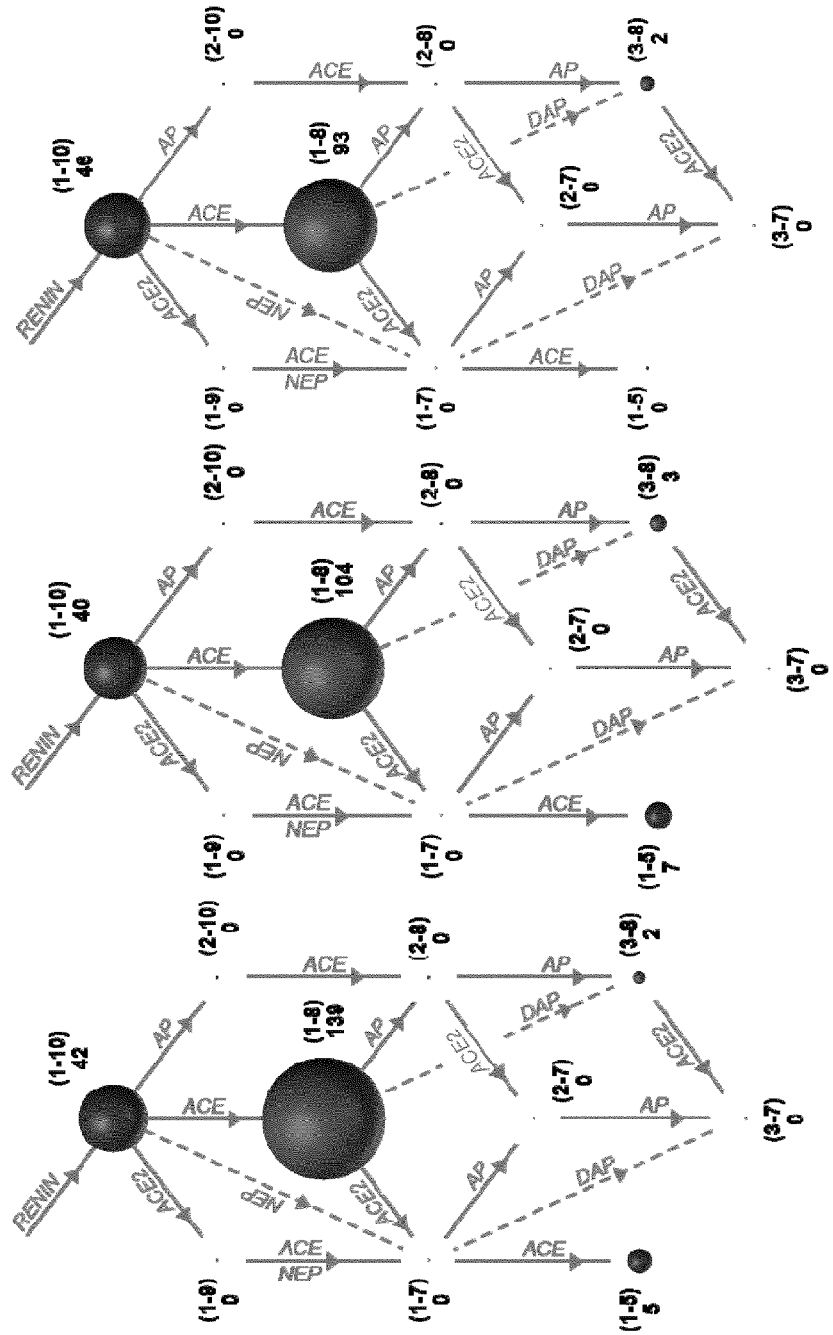
Figure 3B:
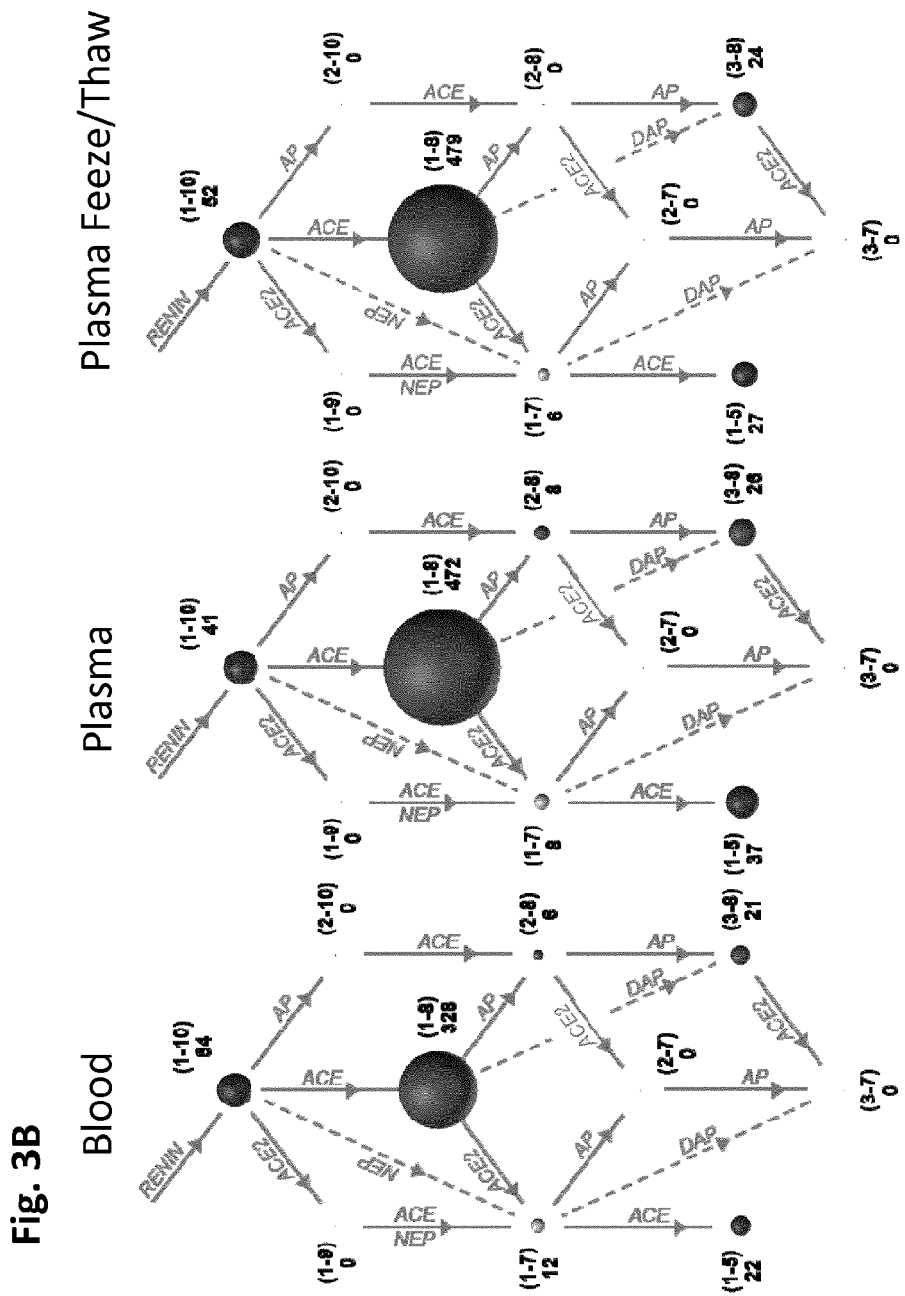

Blood samples were collected and anti-coagulated with standardised heparin tubes (BD). As indicated in FIG. 3, plasma separation has been done for the respective samples before the incubation to reach steady state equilibrium. After incubation of the blood or plasma samples for the time periods as indicated in FIG. 1, or incubation for 2 h for FIGS. 2, 3 and 4, in a 37° C. water bath, samples were cooled on ice followed by immediate addition of the steady state equilibrium conserving protease inhibitor cocktail containing Pepstatin A, 1,10-Phenanthroline, EDTA, p-Hydroxymercuribenzoic acid, and Z-Arg, as well as the internal standards.

LC-MS/MS Sample Preparation and Analysis:

Following plasma separation by centrifugation at 3000 rcf for 10 minutes at 4° C., 0.2-2 ml of plasma was applied onto an activated and equilibrated SEP-PAK™ C18 cartridge. Sample matrix components were removed by washing three times with 1 ml water. Bound analytes were then eluted with 1 ml of methanol. Eluates were evaporated to dryness and reconstituted in 10% acetonitril/90% water supplemented with 0.1% formic acid followed by subjection to LC-MS/MS analysis.

Solid Phase Extraction:

A vacuum manifold has been used for sample processing.
1. Activation EtOH abs.
2. Equilibration 2×1 ml $H_2O$
3. Loading: 0.2-1 ml stabilised plasma
4. Washing: 3×1 ml $H_2O$
5. Elution: 1 ml MeOH Quantification and Signal Integration.

MRM chromatograms were integrated using Analyst 1.5.1 software provided by Applied Biosystems. The threshold for the quantification limit was set at a signal-to-noise ratio of 10. Integration signals not reaching this ratio were set to zero. Analyte signals were related to internal standard signals and concentration was calculated from initially spiked amounts of internal standards.

Results

The evaluation of the RAS in respect to angiotensin peptide concentrations is critically dependent on the conditions used for sample collection and sample conservation. An analytical system was developed which is able to effectively conserve in vivo as well as ex vivo steady state equilibrium angiotensin peptide levels in blood followed by high sensitivity LC-MS/MS-Analysis and absolute quantification.

In general, the RAS is a peptide hormone system constantly producing new peptides from the pro-hormone AGT, whereas the rate of production is primarily dependent on renin activity. The peptide levels, which are present in circulation, are dependent on soluble proteases, blood cell bound proteases and also endothelium associated proteases which can be spatially different due to organ specific expression patterns. The inner surface of blood vessels is covered with numerous different angiotensin receptors and therefore takes over a central part in the establishment of angiotensin peptide concentrations in circulation. As a consequence of organ specific expression of angiotensin metabolising proteases like ACE or ACE2, it becomes obvious that blood peptide levels can be spatially different throughout the body. Nevertheless, there are plenty of enzymatic components of the RAS present in blood either in a freely soluble or in a blood cell associated form, which significantly affect circulating peptide levels. Taking together previous considerations, the RAS constitutes a system with a temporary constant throughput of peptide hormone molecules with local differences regarding peptide concentrations in different tissues and organs.

Figure 1A:
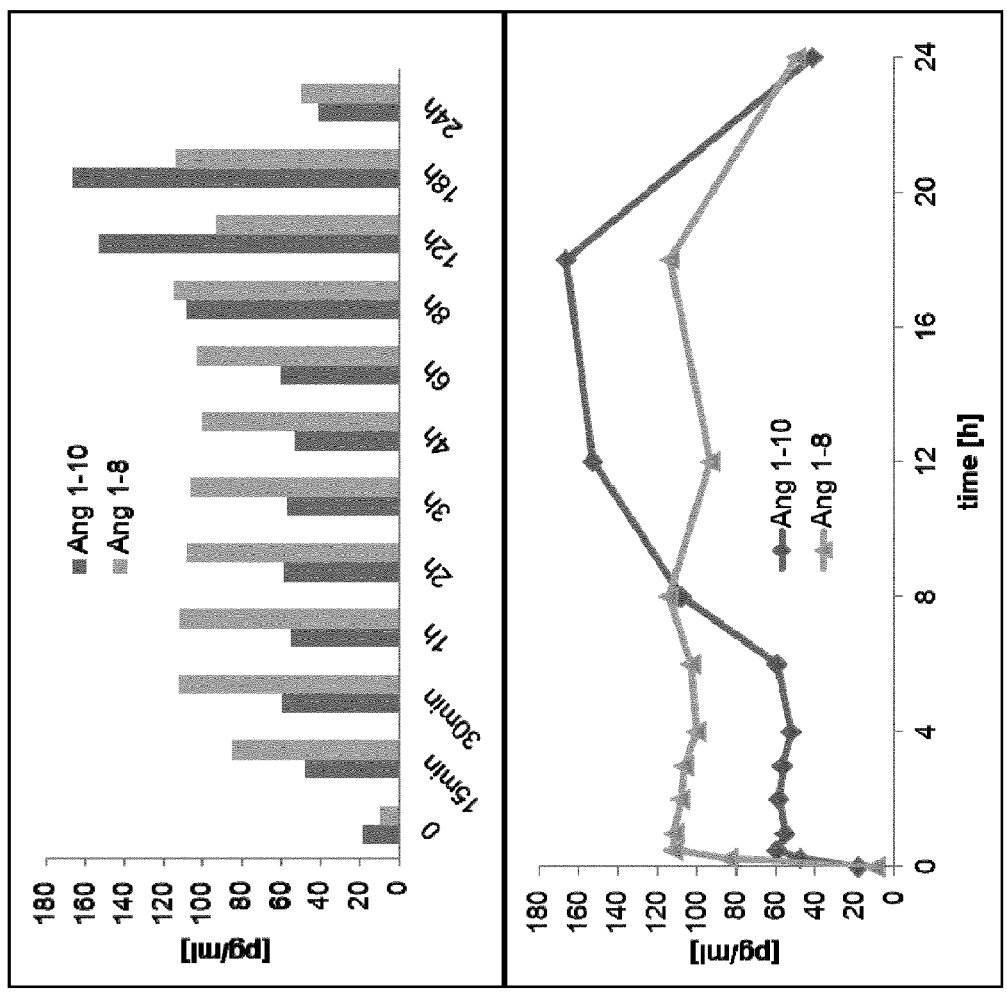
Figure 1B:
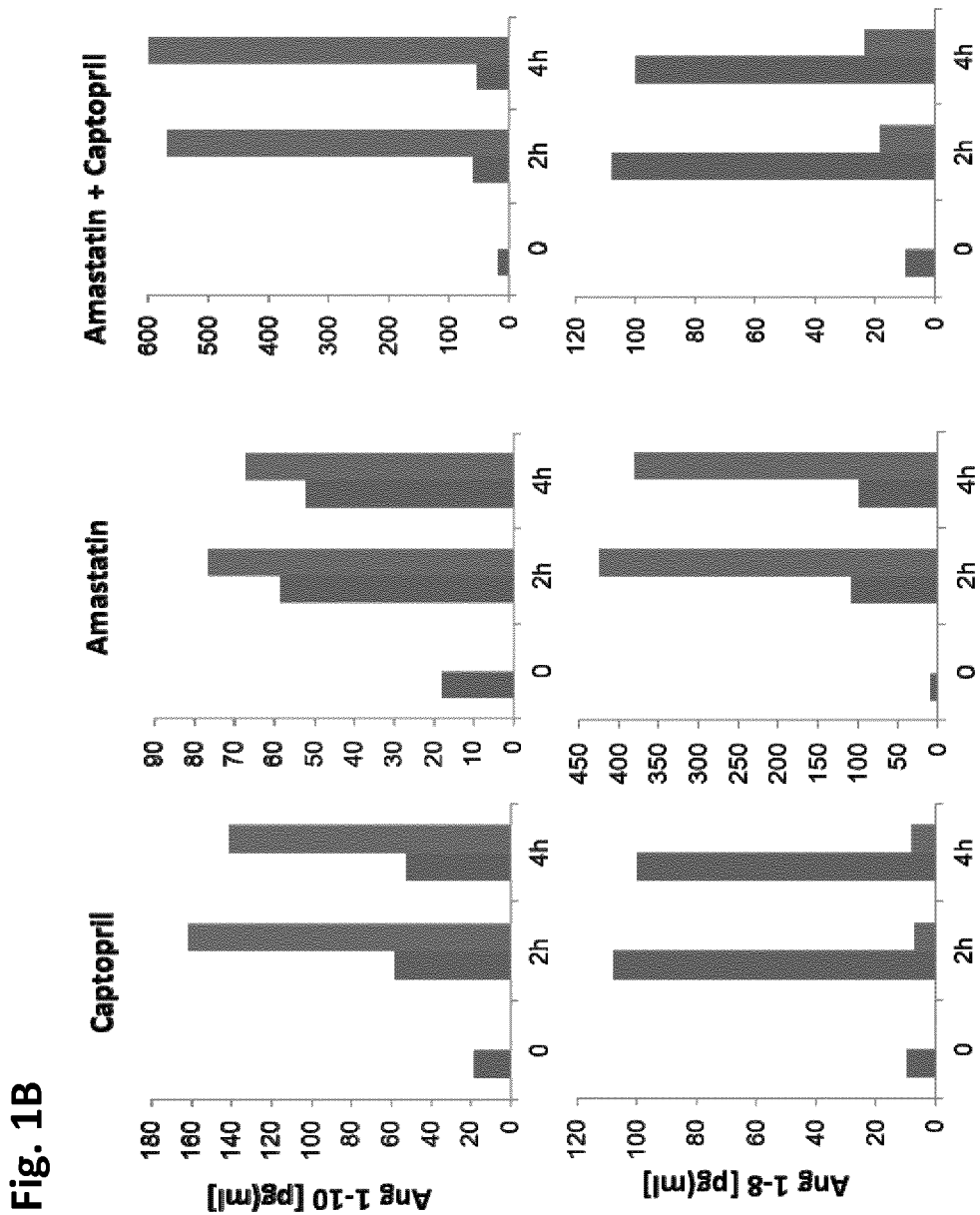

In the present invention a method is described which takes into account all blood associated factors affecting peptide hormone systems like the RAS by incubating a blood or plasma sample until a steady state equilibrium is reached for one or more peptide levels, followed by quantification of peptides. As shown in FIG. 1A, the RAS-Fingerprint which represents the in vivo circulating angiotensin peptide concentrations in blood samples collected by arm venous puncture and immediate sample stabilisation by addition of a protease inhibitor cocktail, is significantly different from the ex vivo RAS-Fingerprint (or RSSE-Fingerprint) observed when blood is incubated at 37° C. without the addition of protease inhibitors. Interestingly, the angiotensin peptide concentrations achieved under these conditions reach levels, which were found to be constant over a remarkable period of time. This indicated a state of equilibrium reached by the sample, which is characterised by equal rates of formation and degradation for individual peptides, namely the steady state equilibrium. The steady state equilibrium peptide levels were reached within 30 minutes and remained stable for at least 6 h from the start of incubation (FIG. 1A). The stability period ended with a strong increase of Ang 1-10 concentration in the sample indicating a change of enzyme activities within the sample. Finally, after 24 h of incubation, the concentration of Ang 1-10 steeply dropped down. Beside Ang 1-10 and Ang 1-8, there were no significant amounts of other angiotensin metabolites detected in the samples during the time course. The so-called RSSE-Fingerprint (RAS steady state equilibrium Fingerprint) was found to be significantly affected by pharmacologic agents interfering with the RAS (FIG. 1B, FIG. 2A). It was further tested if the addition of RAS affecting agents can shift the steady state equilibrium of the sample to a different but stable steady state equilibrium condition. The ACE inhibitor (Captopril) and the aminopeptidase inhibitor (Amastatin) or a combination of both were added to blood prior to incubation for 2 or 4 hours at 37° C. All treatments reached steady state equilibrium characteristic for the inhibitor(s) as indicated by comparable levels of Ang 1-10 and Ang 1-8 after 2 and 4 hours of incubation (FIG. 1B). The ACE inhibitors Lisinopril or Captopril increased the Ang 1-10 and decreased the Ang 1-8 steady state equilibrium levels when compared to control levels. Renin inhibitors, which block the initial step of angiotensin production, were found to completely shut down the RAS. Amastatin, which is an inhibitor of certain aminopeptidases, was found to massively increase Ang 1-8 levels pointing to the important role of aminopeptidases in the regulation of Ang 1-8 levels in vivo.

Figure 1C:
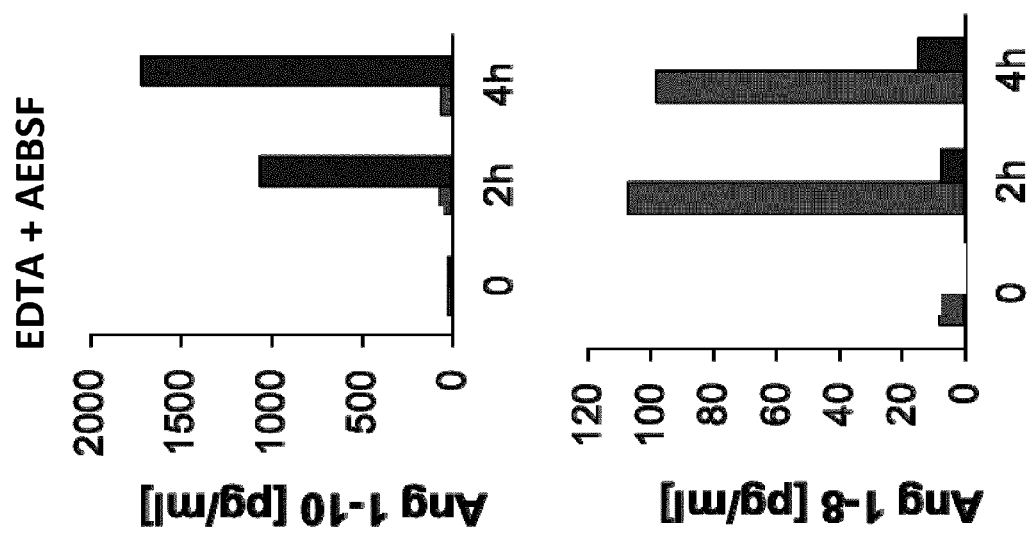

FIG. 1C compares the peptide concentrations reached after 2 h and 4 h incubation at 37° C. in the absence (red bars) and presence of EDTA and AEBSF (blue bars) followed by the conservation of peptide concentrations by addition of an inhibitor cocktail at indicated time points. The combination of EDTA and AEBSF is used in state-of-the-art methods for the measurement of plasma renin activity (PRA) (Bystrom et al.; Clin. Chem. 56(2010), 1561-1569). The concentrations of angiotensin 1-10 (upper panel) and angiotensin 1-8 (lower panel) in control samples reach steady state equilibrium as indicated by minor changes between 2 h and 4 h of incubation at 37° C. (compare FIG. 1B). In contrast, in the presence of EDTA and AEBSF, there are significant changes in the levels of either Ang 1-10 and Ang 1-8 between 2 h and 4 h of incubation at 37° C. The strong accumulation of Ang 1-10 in the EDTA/AEBSF treated sample over time clearly shows the absence of a steady state equilibrium in these samples.

Furthermore, the effects of recombinant RAS enzymes on RSSE-Fingerprints were tested by adding 5 μg/ml ACE, ACE2, NEP, or APN to the samples prior to the incubation periods. The RSSE-Fingerprints shifted as expected in these samples (FIG. 2B) and also in samples where combinations of enzymes with different pharmacologic inhibitors were added (FIG. 2C). Of note, the comparison of samples treated with the ACE inhibitor Lisinopril with the combination of ACE2 and Lisinopril revealed, that Ang 1-10 is a substrate for ACE2 at physiologic concentrations in the original sample matrix, efficiently producing Ang 1-9 (FIG. 2A1, 2C1). Although the steady state levels of Ang 1-10 after addition of ACE2 remain high, there is a remarkable peptide flow in the direction Ang 1-9, which might be an important mechanism of action of ACE inhibitors in clinical use. Furthermore, this ACE2 mediated Ang 1-9 production is impressively shown in the presence of Amastatin, which further increases steady state equilibrium Ang 1-10 levels by inhibiting its N-terminal proteolytic degradation (FIG. 2C3). ACE inhibition was found to be a prerequisite to detect significant steady state equilibrium Ang 1-9 levels which points to a significant higher affinity of Ang 1-10 to ACE than to ACE2. This higher affinity of Ang 1-10 to ACE than to ACE2 could also be confirmed by the observation of lower steady state equilibrium Ang 1-10 concentrations comparing addition of ACE to ACE2 (FIG. 2B1).

The results obtained from these experiments clearly demonstrated a direct association of the RSSE-Fingerprint with the integrated RAS enzyme activities contained in the sample.

Figure 3C:
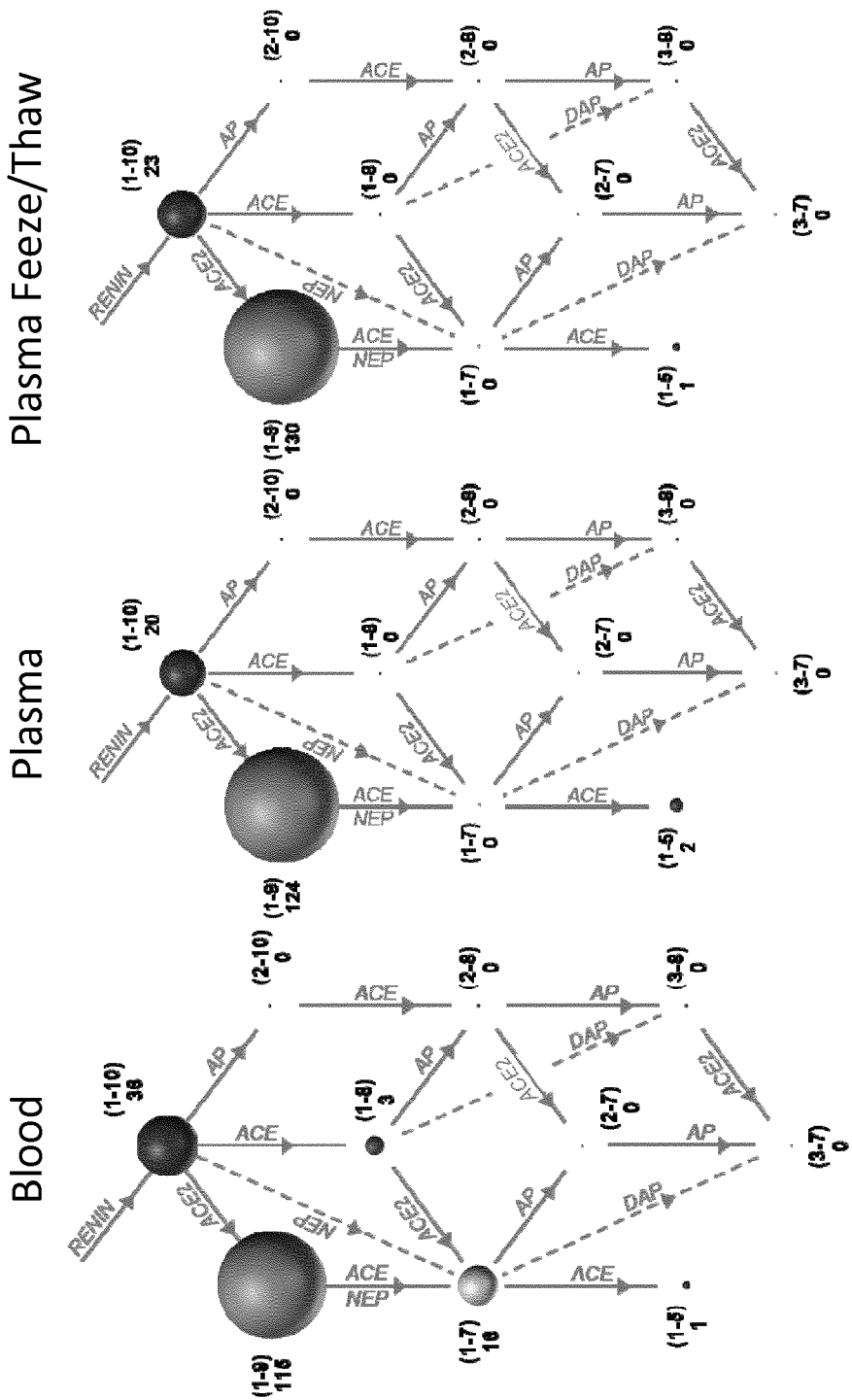

Based on these findings, the effect of using fresh or frozen plasma instead of blood were explored as there would be easier handling regarding large scale analysis, knowing that blood cell associated RAS components would be lost under these conditions. The RSSE-Fingerprints were compared for blood, plasma and frozen/thawed plasma from the same donor for control samples (FIG. 3A), Amastatin spiked samples (FIG. 3B) and samples spiked with ACE2 and Lisinopril (FIG. 3C). The inhibitors and combinations were selected in order to achieve a clearly visible shift of the steady state equilibrium while using either enzymes or low molecular weight inhibitors to proof the method's suitability for clinical analytic questions. Freezing and thawing of plasma was found to cause minimal variations in the RSSE-Fingerprint whereas using blood instead of plasma resulted in significant differences especially regarding Ang 1-10, Ang 1-8 and Ang 1-7 which point to the presence of blood cell associated NEP (CD10) and ACE (CD143).

Figure 4A:
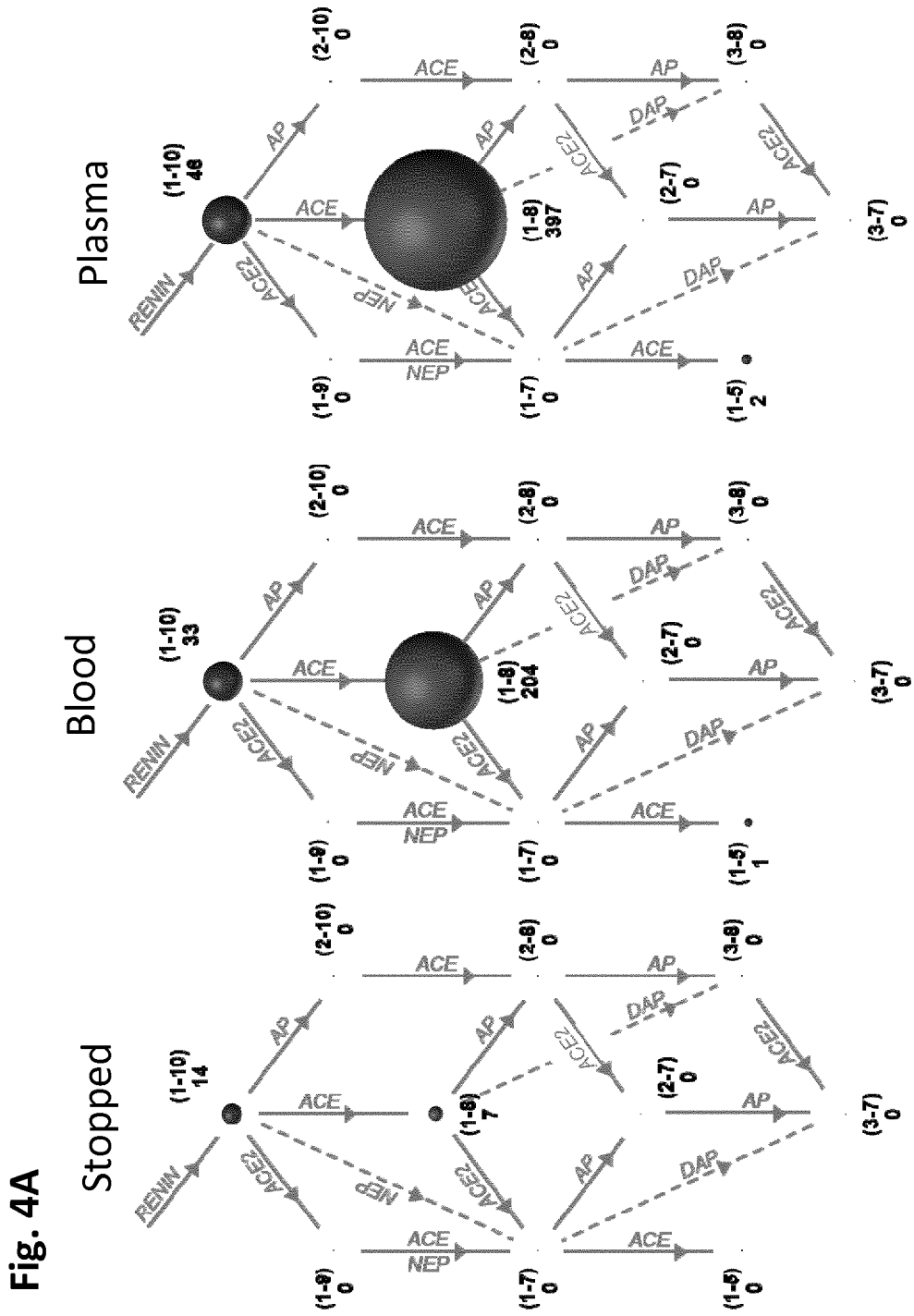

Finally the variability of the RAS-Fingerprint and the RSSE-Fingerprint was investigated among 12 healthy volunteers and analysed in immediately stabilised blood, equilibrated blood and equilibrated plasma from each donor. The mean of the measured angiotensin concentrations is given as a fingerprint graph in FIG. 4A. Donor specific data regarding Ang 1-10 and Ang 1-8, which are the predominant peptide present in healthy volunteers, are given for the RAS-Fingerprints (4B1—Table 1), the RSSE-Fingerprint in blood (4B2—Table 2) as well as the RSSE-Fingerprint in plasma (4B3—Table 3). Beside concentrations of the peptides in pg/ml, the concentrations were calculated in fmol/ml and used to constitute a molar steady state activity ratio for ACE by dividing the Ang 1-8 concentration through the Ang 1-10 concentration. Compared to the RAS-Fingerprints measured, the RSSE-Fingerprints showed greater variances among donors, which reflect potential diversities in the constitution of the soluble RAS components among different donors. Two representative donors are shown in FIG. 4C. Donor 3 (FIG. 4C1) had a molar SSE-Ratio for ACE in blood (1-8/1-10) of 4.5 while Donor 6 (FIG. 4C2) displayed an ACE-SSE-Ratio of 20.5 pointing to a more prominent role of ACE in the production of Ang 1-8 in this donor. There is also a difference in the RAS-ratio for ACE (0.35 vs. 0.79), however, the difference based on the RSSE-Fingerprint are much more distinctive.

As a conclusion, a powerful method for the evaluation of the RAS or components thereof in biological samples is provided with the present invention. The combination of the present highly sensitive LC-MS/MS based angiotensin peptide quantification method with the innovative steady state equilibration of the sample prior to stabilisation represents a highly reproducible tool for evaluation of soluble and blood cell associated RAS enzyme activities. The use of this new technology has a great potential for the discovery of biomarkers as the RAS is involved in a variety of pathologic conditions. Furthermore, soluble and blood cell associated RAS enzyme activities represent a major site of pharmacologic activity of several anti-hypertensive drugs. The understanding of the system's individuality might pave the way for patient specific approaches in the treatment of RAS associated diseases. The technology according to the present invention will push this development forward by providing a deep and comprehensive insight into the renin-angiotensin system in biological samples.

Example II: Analysis of Proteolytic Cascade Degradation Products of the Renin-Angiotensin System as Well as the Bradykinin System in Blood Samples According to the Present Invention All methods were done as described in Example I, except that the plasma samples were stabilised by the addition of 4M GTC/1% TFA, either immediately or after incubation for 1 or 3 hours in a 37° C. water bath.

Results

Figure 7A:
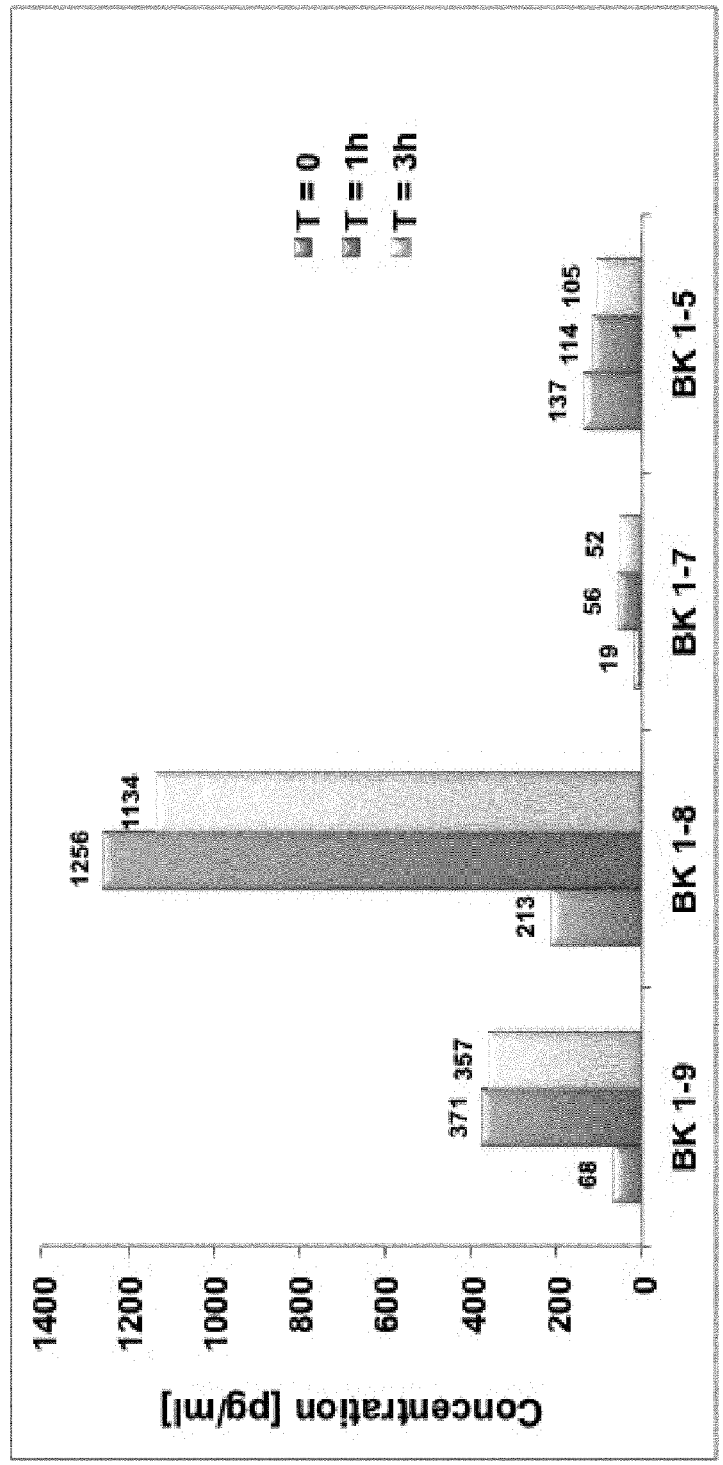
FIG. 7 shows the respective bar graphs.

FIGS. 6 and 7 show that the method according to the present invention can be applied not only to the RAS, but also to other proteolytic cascades, such as the bradykinin system. Furthermore, these figures show that the steady state equilibrium can efficiently be stabilised not only by the addition of a protease inhibitor cocktail, but also by a chaotropic agent such as GTC. After an incubation period of 1 h, a steady state equilibrium has been reached for the RAS and the bradykinin system and remained stable, as can be seen from the comparison of peptide levels between 1 h and 3 h of incubation.

The invention claimed is:

1. A method for measurement of peptidic degradation products of a proteolytic cascade comprising at least two consecutive proteolytic reactions in a biological sample comprising:

incubating a biological sample ex vivo until the actual overall degradation rate of at least one peptidic degradation product is equal to the actual overall formation rate of the at least one peptidic degradation product and a steady state equilibrium is reached for the at least one peptidic degradation product involved in the proteolytic cascade; and quantifying at least one peptidic degradation product in a steady state equilibrium concentration in the sample, wherein the method further comprises adding one or more protease inhibitor and/or one or more chaotropic agent after the incubation until a steady state equilibrium is reached for at least one peptidic degradation product, and wherein substrates of any enzyme(s) involved in the proteolytic cascade are not added before and/or during the incubation until a steady state equilibrium is reached.

2. The method of claim 1, wherein the sample is a blood sample.

3. The method of claim 2, where the blood sample comprises full blood, plasma, serum, fresh or frozen anti-coagulated full blood, or fresh or frozen anti-coagulated plasma.

4. The method of claim 1, wherein at least two degradation products of the proteolytic cascade are quantified in the sample in steady state equilibrium concentration.

5. The method of claim 4, wherein a ratio is calculated of the steady state equilibrium quantifications of the at least two peptidic degradation products.

6. The method of claim 1, wherein the sample is incubated for up to 300 minutes.

7. The method of claim 1, wherein the sample is incubated at a temperature of 30 to 50° C.

8. The method of claim 1, wherein the proteolytic cascade is a renin-angiotensin system (RAS) or a bradykinin system, or both.

9. The method of claim 1, wherein the peptidic degradation product is angiotensinogen, angiotensin I (Ang 1-10), angiotensin 2-10 (Ang 2-10), angiotensin II (angiotensin 1-8 or Ang 1-8), angiotensin III (angiotensin 2-8 or Ang 2-8), angiotensin IV (angiotensin 3-8 or Ang 3-8), angiotensin 1-9 (Ang 1-9), angiotensin 1-7 (Ang 1-7), angiotensin 2-7 (Ang 2-7), angiotensin 3-7 (Ang 3-7), angiotensin 1-5 (Ang 1-5), kallidin (KD or Lys-bradykinin), bradykinin 1-9 (BK 1-9), bradykinin 2-9 (BK 2-9), bradykinin 1-8 (BK 1-8), bradykinin 1-7 (BK 1-7), or 1-5 (BK 1-5).

10. The method of claim 1, further defined as comprising quantifying angiotensin I (1-10), angiotensin II (angiotensin 1-8 or Ang 1-8), angiotensin 1-7 (Ang 1-7), and angiotensin 1-5 (Ang 1-5).

11. The method of claim 1, further defined as comprising quantifying angiotensin II (angiotensin 1-8 or Ang 1-8), angiotensin 1-7 (Ang 1-7), and angiotensin 1-5 (Ang 1-5).

12. The method of claim 1, further defined as comprising quantifying bradykinin 1-9 (BK 1-9), bradykinin 1-8 (BK 1-8), bradykinin 1-7 (BK 1-7) and bradykinin 1-5 (BK 1-5).

13. The method of claim 1, further defined as comprising quantifying bradykinin 1-8 (BK 1-8), bradykinin 1-7 (BK 1-7) and bradykinin 1-5 (BK 1-5).

14. A physical or electronic representation of the result of quantification of the method of claim 1, comprising at least two quantified amounts of the at least two degradation products provided in sequence of the proteolytic cascade.

15. The physical or electronic representation of claim 14, comprising quantified amounts of at least two of angiotensin I (Ang 1-10), angiotensin 2-10 (Ang 2-10), angiotensin II (angiotensin 1-8 or Ang 1-8), angiotensin III (angiotensin 2-8 or Ang 2-8), angiotensin IV (angiotensin 3-8 or Ang 3-8), angiotensin 1-9 (Ang 1-9), angiotensin 1-7 (Ang 1-7), angiotensin 2-7 (Ang 2-7), angiotensin 3-7 (Ang 3-7), angiotensin 1-5 (Ang 1-5), kallidin (KD or Lys-bradykinin), bradykinin 1-9 (BK 1-9), bradykinin 2-9 (BK 2-9), bradykinin 1-8 (BK 1-8), bradykinin 1-7 (BK 1-7), and bradykinin 1-5 (BK 1-5) in dependence of their relative quantities.

16. The physical or electronic representation of claim 15, comprising quantified amounts of angiotensin I (Ang 1-10), angiotensin 2-10 (Ang 2-10), angiotensin II (angiotensin 1-8 or Ang 1-8), angiotensin III (angiotensin 2-8 or Ang 2-8), angiotensin IV (angiotensin 3-8 or Ang 3-8), angiotensin 1-9 (Ang 1-9), angiotensin 1-7 (Ang 1-7), angiotensin 2-7 (Ang 2-7), angiotensin 3-7 (Ang 3-7), and angiotensin 1-5 (Ang 1-5) in dependence of their relative quantities.

17. The physical or electronic representation of claim 15, comprising quantified amounts of kallidin (KD or Lys-bradykinin), bradykinin 1-9 (BK 1-9), bradykinin 2-9 (BK 2-9), bradykinin 1-8 (BK1-8), bradykinin 1-7 (BK 1-7), and bradykinin 1-5 (BK 1-5) in dependence of their relative quantities.

18. The method of claim 1, wherein the at least one steady state equilibrium peptide level does not vary more than 15% over a time period of at least 30 minutes.

19. The method of claim 1, wherein at least one of the at least two proteolytic reactions is performed by a feeding enzyme, said feeding enzyme having a turnover rate, and wherein the turnover rate of the feeding enzyme does not vary more than 15% over a time period of at least 30 minutes.

\* \* \* \* \*